United States Patent
Siess et al.

(10) Patent No.: US 10,786,509 B2
(45) Date of Patent: Sep. 29, 2020

(54) TREATMENT AND PREVENTION OF ATHEROTHROMBOSIS BY INHIBITION OF BRUTON'S TYROSINE KINASE (BTK)

(71) Applicant: Wolfgang Siess, Munich (DE)

(72) Inventors: Wolfgang Siess, Munich (DE); Kristina Busygina, Munich (DE)

( * ) Notice: Subject to any disclaimer, the term of this patent is extended or adjusted under 35 U.S.C. 154(b) by 0 days.

(21) Appl. No.: 16/314,370

(22) PCT Filed: Jun. 30, 2017

(86) PCT No.: PCT/EP2017/066302
§ 371 (c)(1),
(2) Date: Dec. 28, 2018

(87) PCT Pub. No.: WO2018/002316
PCT Pub. Date: Jan. 4, 2018

(65) Prior Publication Data
US 2019/0151321 A1    May 23, 2019

(30) Foreign Application Priority Data

Jun. 30, 2016 (LU) .......................................... 93133

(51) Int. Cl.
| | |
|---|---|
| *A61P 9/10* | (2006.01) |
| *A61P 7/02* | (2006.01) |
| *A61K 31/519* | (2006.01) |
| *A61K 31/4985* | (2006.01) |
| *A61K 31/522* | (2006.01) |
| *A61K 31/7105* | (2006.01) |
| *C07K 16/40* | (2006.01) |
| *C12N 15/113* | (2010.01) |

(52) U.S. Cl.
CPC ........ *A61K 31/519* (2013.01); *A61K 31/4985* (2013.01); *A61K 31/522* (2013.01); *A61K 31/7105* (2013.01); *A61P 7/02* (2018.01); *A61P 9/10* (2018.01); *C07K 16/40* (2013.01); *C12N 15/1137* (2013.01); *C07K 2317/76* (2013.01); *C12N 2310/11* (2013.01); *C12N 2310/12* (2013.01); *C12N 2310/122* (2013.01); *C12N 2310/14* (2013.01); *C12N 2310/141* (2013.01); *C12N 2310/16* (2013.01); *C12N 2310/531* (2013.01)

(58) Field of Classification Search
None
See application file for complete search history.

(56) References Cited

U.S. PATENT DOCUMENTS 6,589,992 B2    7/2003 Uckun

OTHER PUBLICATIONS

Parnnar et al, 2014. P&T. 39(7): 483-487 and 519 (6 pages total).*
Rigg, Rachel et al.: "Oral administration of Bruton's tyrosine kinase inhibitors impairs GPVI-mediated platelet function", American Journal of Physiology—Cell Physiology, vol. 310, No. 5, pp. C373-C380. Accepted Dec. 9, 2015 (Dec. 9, 2015), published Mar. 1, 2016.
Tibbles, Heather E. et al.: "In vivo toxicity and antithrombotic profile of the oral formulation of the antileukemic agent, LFM-A13-F", Arzneimittel Forschung. Drug Research, ECV Editto Cantor Verlag, Aulendorf, DE, vol. 54, No. 6, Jan. 2004 (Jan. 2004), pp. 330-339.
Penz, Sandra et al.: "Human atheromatous plaques stimulate thrombus formation by activating platelet glycoprotein VI", The FASEB Journal, Federation of American Societies for Experimental Biology, US, vol. 19, No. 8, Jun. 2005 (Jun. 2005), pp. 898-909.
Byrd, John C. et al.: "Acalabrutinib (ACP-196) in Relapsed Chronic Lymphocytic Leukemia", New England Journal of Medicine (NEJM,) Dec. 7, 2015 (Dec. 7, 2015).
WNhang, Jennifer A. et al.: "Bruton's tyrosine kinase inhibitors for the treatment of rheumatoid arthritis", Drug Discovery Today,vol. 19, No. 8, Apr. 12, 2014 (Apr. 12, 2014), pp. 1200-1204.
Tam, Constantine et al.: "The BTK Inhibitor, Bgb-3111, Is Safe, Tolerable, and Highly Active in Patients with Relapsed/Refractory B-Cell Malignancies: Initial Report of a Phase 1 First-in-Human Trial" Accession No. PREV201600270707, BIOSIS, Dec. 1, 2015 Biosciences Information Service, Philadelphia, PA, US ("Tam_et_al_Abstract_Blood_2015").
Tam, Constantine et al.: "The BTK Inhibitor, Bgb-3111, Is Safe, Tolerable, and Highly Active in Patients with Relapsed/Refractory B-Cell Malignancies: Initial Report of a Phase 1 First-in-Human Trial" Blood vol. 126, No. 23, Dec. 2015 (Dec. 2015), 57th Annual Meeting of the American-Society-of-Hematology; Orlando, FL, USA; Dec. 5-8, 2015 ("Tam_et_al_Blood_Journal_2015").

* cited by examiner

*Primary Examiner* — Zachary C Howard
(74) *Attorney, Agent, or Firm* — Perdue IP Law, APC

(57) ABSTRACT

The present invention relates to an inhibitor of Bruton's tyrosine kinase (Btk) for use in the treatment and/or prevention of atherothrombosis. The present invention further relates to a method of treating and/or preventing atherothrombosis comprising administering a pharmaceutically effective amount of an inhibitor of Bruton's tyrosine kinase (Btk) to a subject in need thereof.

5 Claims, 26 Drawing Sheets

Figure 1:
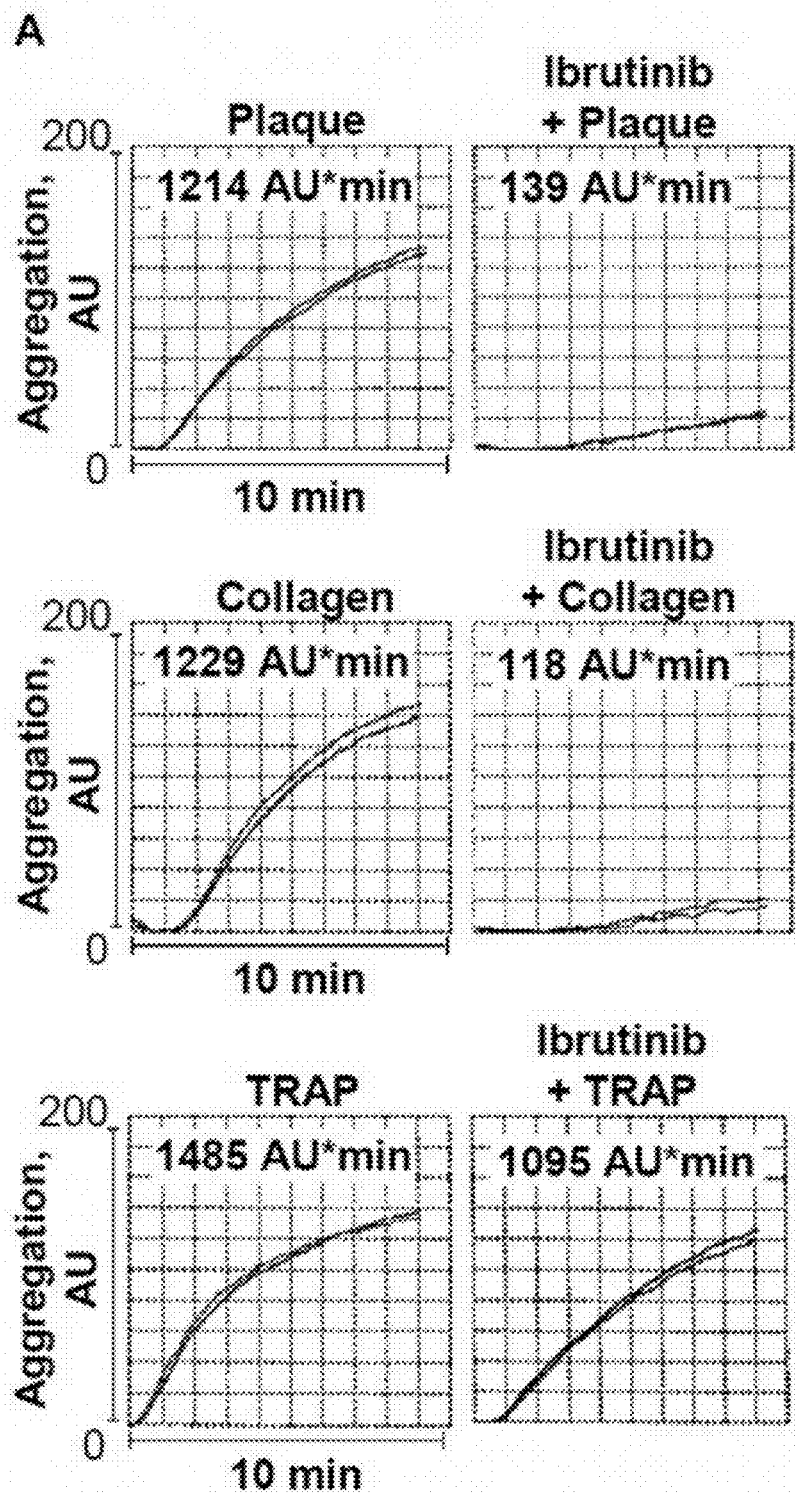
Figure 1:
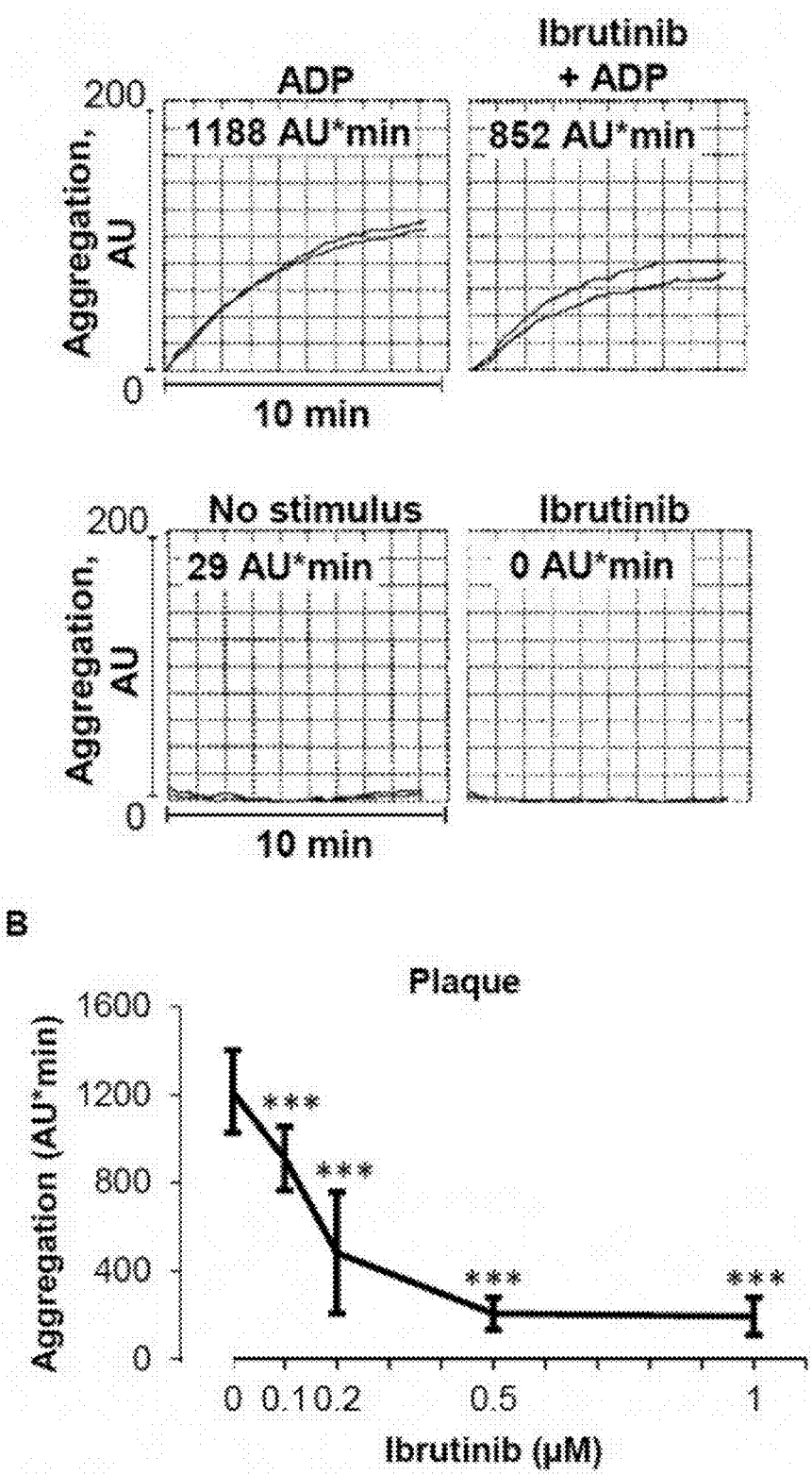
Figure 1:
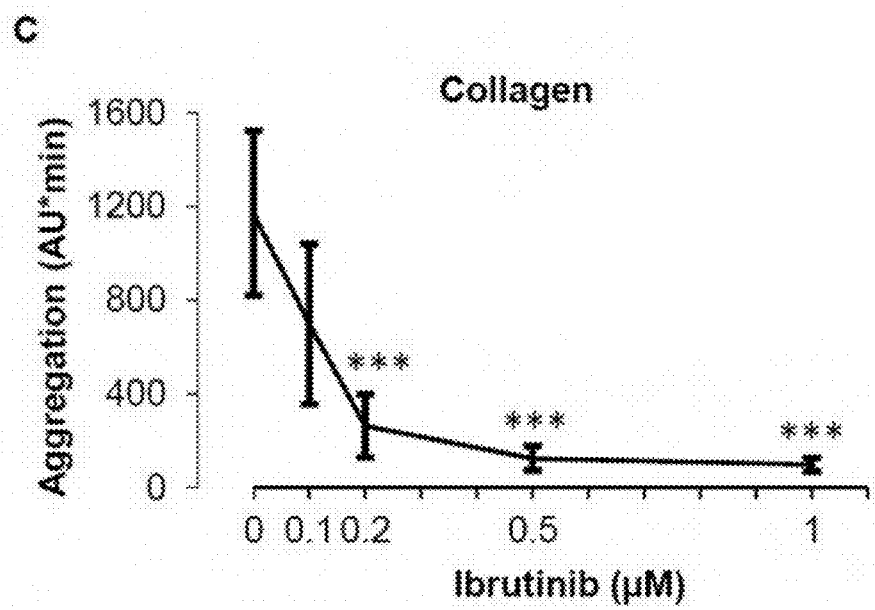
Figure 1:
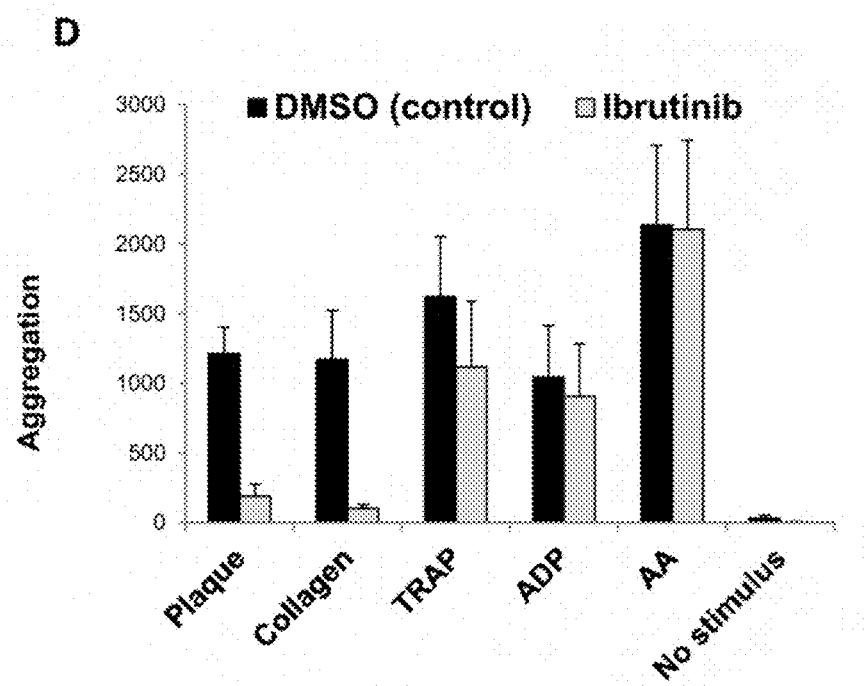

TREATMENT AND PREVENTION OF ATHEROTHROMBOSIS BY INHIBITION OF BRUTON'S TYROSINE KINASE (BTK)

CROSS-REFERENCE TO RELATED APPLICATIONS

This application is a national stage application under 35 U.S.C. § 371, of International Application No. PCT/EP2017/066302, filed Jun. 30, 2017, which claims benefit of priority to Luxembourg (LU) Patent Application No. 93133, filed Jun. 30, 2016, each of which is incorporated herein by reference in its entirety.

The present invention relates to an inhibitor of Bruton's tyrosine kinase (Btk) for use in the treatment and/or prevention of atherothrombosis. The present invention further relates to a method of treating and/or preventing atherothrombosis comprising administering a pharmaceutically effective amount of an inhibitor of Bruton's tyrosine kinase (Btk) to a subject in need thereof.

In this specification, a number of documents including patent applications and manufacturer's manuals is cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Vessel wall injury results in the activation of platelets and formation of a platelet plug, followed by further coagulant activity, that leads to the formation of fibrin-containing thrombi which occlude the injured vessel. Haemostasis is thus an event that begins with the adherence of platelets to activating components of the subendothelial matrix, such as collagen. Similarly, the erosion or rupture of an atherosclerotic plaque results in the formation of a platelet- and fibrin-rich thrombus, by arresting circulating platelets on the exposed material, such as extracellular matrix components. Whereas normal haemostasis is an important function, the thrombus formation due to erosion or rupture of an atherosclerotic plaque can be detrimental, as it can lead to myocardial infarction and ischemic stroke, two of the leading causes of death worldwide (Fuster V. et al., *J Am Coll Cardiol*. 2005; 46:937-954; Badimon L. and Vilahur G. *J Int Med* 2014; 276:618-632).

Fibrous collagens are reactive matrix components that are of particular importance in platelet adhesion and activation. Several platelet collagen receptors have been identified so far, of which especially glycoprotein VI (GPVI) and glycoprotein Ia-IIa (integrin α2β1) are currently considered to be clinically important. Kuijpers M J E. et al. (*FASEB Journal* 2003; 17(6):685-687) investigated the roles of these two important collagen receptors GPVI and integrin α2β1 on platelets, as well as the role of $G\alpha_q$ heterotrimer signaling in platelet responses evoked by $TxA_2$ and ADP through the TPα and P2Y1 receptors, respectively. Their findings indicated that initial platelet tethering to—collagen exposed to flowing blood critically involves the interaction between GPIb and von Willebrand factor deposited from plasma on the collagen, and that stable platelet-collagen adhesion under high wall shear rates ($>500$ $s^{-1}$) depends on both integrin α2β1 and active GPVI receptors. It was hypothesised that platelet binding and activation via GPVI primes the cells for integrin-mediated adhesion, and that activated integrin α2β1 stabilises the platelets on collagen. The authors concluded that agents inhibiting integrin α2β1, potentially in combination with anti-GPVI effects, could be useful for platelet-directed antithrombotic therapies.

In Auger et al. (*FASEB Journal* 2005; 19(7):825-827 and full article as published in the World Wide Web under fasebj.org/cgi/doi/10.1096/fj.04-1940fje), the authors noted that there are certain controversies in the literature about the individual roles of integrin α2β1 and GPVI in the adhesion of platelets on collagen. The aim of said study was thus to carry out experiments to address these controversies. To this end, both human and mouse platelets were analysed under the same experimental conditions, using identical or equivalent experimental tools. The authors found that there are two distinct pathways of stable adhesion, one based on activation of GPVI and Src family kinases and the other being dependent on integrin α2β1. Auger et al. further found that integrin α2β1 was capable of mediating adhesion of mouse platelets in the absence of GPVI expression or downstream Src kinase activity and intracellular calcium elevation.

Because the composition of plaque material differs from the composition of healthy vessels, one aspect under investigation was, and still is, the precise nature of these compositions and their influence on thrombus formation. Work that focused on thrombus formation using a model simulating the rupture of human lipid-rich atherosclerotic plaques (Penz et al. *FASEB Journal* 2005; 19(7):898-909) revealed the presence of morphologically altered collagen type I- and type III-positive structures in the plaques. The authors of this work found that inhibition of GPVI with the antibody 10B12, which specifically binds the collagen-binding site of GPVI, completely blocked platelet thrombus formation onto plaques in flowing blood, whereas no effect by antibody-mediated inhibition of integrin α2β1 was observed. This work was confirmed and expanded in Schulz et al. (*Basic Res Cardiol*. 2008; 103:356-367), where the binding to type I- and III-containing structures was further investigated, using a different anti-GPVI antibody (5C4). The authors of these two studies concluded that the morphologically diverse collagen type I- and type III-containing structures in the plaques stimulate the thrombus formation by activating platelet GPVI, and that inhibition of GPVI might provide a novel antithrombotic strategy to prevent atherothrombosis in patients at cardiovascular risk. Further studies into the inhibition of atherosclerotic plaque-induced platelet activation by using dimeric GPVI-Fc or various anti-GPVI antibodies were described in Jamasbi et al. (*J Am Coll Cardiol*. 2015; 65:2404-2415). The authors suggested that the use of GPVI-Fc would be preferable for therapy, because there are concerns that antibodies could potentially induce immune responses and may increase bleeding, although no such detrimental immune responses or increased bleeding effects were shown for the antibodies employed in this study.

An alternative approach has been described in Penz et al. (*Thromb Haemost*. 2007; 97:435-443), where the authors focused on GPIbα, the platelet receptor that interacts with von Willebrand factor (VWF) present on plaque collagen structures. This interaction is thought to represent the first step in thrombus formation, inducing initial platelet tethering and transient adhesion. The authors found that under flow conditions with high shear rates of 1.500 $s^{-1}$, contrary to static conditions, aspirin failed to significantly inhibit plaque-induced thrombus formation, and a combination of $P2Y_1$ and $P2Y_{12}$ receptor antagonists (ADP receptor antagonists) was less effective in reducing plaque-stimulated platelet thrombus formation than the blocking of GPIbα. Thus, the authors concluded that VWF might play an important role in platelet thrombus formation after plaque rupture and suggested that a combination of different anti-platelet drugs, such as P2Y$_1$/P2Y$_{12}$ receptor antagonists and inhibitors of GPIbα or GPVI might improve the prevention of human plaque-induced thrombus formation after plaque rupture.

As shown above, numerous studies have been carried out to elucidate the mechanism of platelet activation and aggregation, both in healthy vessels as well as in a model simulating the rupture of atherosclerotic plaques. However, despite the fact that a lot of effort is currently being invested into these studies, the most common therapy at present is still a dual anti-platelet therapy with aspirin and a P2Y12-antagonist. Although this therapy reduces ischemic cardiovascular events, its efficacy is limited and, most importantly, this therapy has the drawback of being associated with an increased bleeding risk (Bonaca M P. et al., *N Engl J Med.* 2015; 372:1791-1800), as these compounds target not only plaque-triggered platelet activation, but also affect physiologic haemostatic mechanisms. Thus, novel therapies aiming specifically at plaque-triggered platelet activation with high efficacy but that leave physiologic haemostatic mechanisms intact would offer tremendous value to the field.

This need is addressed by the provision of the embodiments characterised in the claims.

Accordingly, the present invention relates to an inhibitor of Bruton's tyrosine kinase (Btk) for use in the treatment and/or prevention of atherothrombosis.

The term "Bruton's tyrosine kinase", also abbreviated as Btk herein, refers to a tyrosine kinase that in humans is encoded by the BTK gene. The human Btk protein has the NCBI Reference Sequence: NP_000052.1 (last updated Jan. 5, 2016) and the encoding mRNA has the NCBI Reference Sequence: NM_000061.2 (also last updated Jan. 5, 2016). Btk plays a key role in development of pre-B cells and B-lymphocytes by connecting receptors to the elevation of intracellular-free calcium levels. Btk-inhibitors such as ibrutinib inhibit B-cell function and proliferation.

Ibrutinib and other compounds which inhibit Btk activity are also known to inhibit platelets. Btk plays a key role in collagen/GPVI and VWF/GPIb triggered platelet signal transduction pathways (Quek L S. et al., *Current biology: CB.* 1998; 8:1137-1140; Oda A. et al., *Blood.* 2000; 95:1663-1670; Liu J. et al, *Blood.* 2006). Upon platelet GPIb engagement by VWF and GPVI stimulation by collagen, the tyrosine kinases Lyn and Syk are first activated, thereby initiating the assembly of a signaling complex of adapter proteins and enzymes including Btk and PLCγ2 (Liu J. et al, *Blood.* 2006; 108:2596-260; Watson S P. et al., *J Thromb Haemost.* 2005; 3:1752-176). Btk is phosphorylated by Syk and Lyn, is further auto-phosphorylated, and participates in the tyrosine phosphorylation and activation of the effector protein PLCγ2 (Quek L S. et al., *Current biology* 1998; 8:1137-1140; Watson S P. et al., *J Thromb Haemost.* 2005; 3:1752-176; Liu J. et al, *Blood.* 2006; 108:2596-260), which leads to cytosolic Ca$^{2+}$ increase and protein kinase C activation, the two main downstream signaling pathways for platelet activation (Siess W. *Physiol Rev.* 1989; 69:58-178). In addition, it has been reported that platelet integrin αIIbβ3 outside-in signaling during thrombin-induced platelet aggregation stimulates Btk (Laffargue M et al *FEBS Letters* (1999) 443: 66-70). The platelet integrin αIIbβ3 is the main fibrinogen receptor and essential for platelet aggregation.

Accordingly ibrutinib has been found to inhibit collagen and von VWF-dependent platelet functions in static assays and under arterial flow in vitro and ex vivo in patients treated with ibrutinib (Levade M. et al. *Blood.* 2014; 124:3991-3995; Kamel S. et al. *Leukemia.* 2015; 29:783-787; Kazianka L. et al *Leukemia* (2016), 1-6). Some of the platelet functions studied after ibrutinib addition in vitro or in ibrutinib-treated patients ex vivo was inhibition of collagen- or CRP- (a GPVI-agonist) stimulated platelet aggregation in PRP, ristocetin-induced platelet aggregation in blood (ristocetin mediates binding of VWF to GPIb), and collagen- and vWF-induced platelet thrombus formation in flowing blood (Levade M. et al. *Blood.* 2014; 124:3991-3995; Kamel S. et al. *Leukemia.* 2015; 29:783-787; Kazianka L. et al *Leukemia* (2016), 1-6; Bye A P et al. *Arterioscler. Thromb. Vasc. Biol.* (2015), 35(11):2326-35). Ibrutinib has been also shown to inhibit platelet integrin αIIbβ3 outside-in signaling, and subsequent platelet adhesion and spreading onto immobilized fibrinogen in vitro (Bye A P et al. *Arterioscler Thromb Vasc Biol* (2015), 35(11):2326-35). The inhibitory effects of ibrutinib on collagen- and VWF/GPIb-mediated platelet responses had been associated with the increased bleeding risk of patients taking ibrutinib compared with standard chemotherapy (Levade M. et al. *Blood.* 2014; 124:3991-3995; Kamel S. et al. *Leukemia.* 2015; 29:783-787; Kazianka L. et al *Leukemia* (2016), 1-6; Shatzel J J et al. *J Thromb Haemostas* (2017), 15: 1-13). Interestingly, treatment of patients with new, more selective BTK inhibitors (second-generation BTK inhibitors such as ACP-196, ONO/GS-4059, and BGB-3111) apparently increases the bleeding risk less than treatment of patients with ibrutinib (Wu J et al *J Hematol Oncol* (2016) 9:80). Also the new Btk inhibitors BTKI-43607 and BTKI-43761 orally administered to non-human primates for 10 days did not show an increase of template skin bleeding time or an effect on coagulation (Rigg R A, et al. *Am J Physiol Cell Physiol.* 2016; 310:C373-380).

The term "inhibitor" in accordance with the present invention refers to an inhibitor that reduces or abolishes the biological function or activity of a particular target protein. An inhibitor may perform any one or more of the following effects in order to reduce or abolish the biological function or activity of the protein to be inhibited: (i) the transcription of the gene encoding the protein to be inhibited is lowered, i.e. the level of mRNA is lowered, (ii) the translation of the mRNA encoding the protein to be inhibited is lowered, and (iii) the protein performs its biochemical and/or cellular function with lowered efficiency in the presence of the inhibitor. Compounds falling in class (i) include compounds interfering with the transcriptional machinery and/or its interaction with the promoter of said gene and/or with expression control elements remote from the promoter such as enhancers. Compounds of class (ii) comprise antisense constructs and constructs for performing RNA interference (e.g. siRNA) well known in the art (see, e.g. Zamore (2001) *Nat Struct Biol.* 8(9), 746; Tuschl (2001) *Chembiochem.* 2(4), 239). Compounds of class (iii) interfere with the molecular function of the protein to be inhibited, such as receptor signaling activity and activation of downstream target molecules. Accordingly, active site binding compounds are envisaged. Class (iii) also includes compounds which do not necessarily bind directly to the target, but still interfere with its function or activity, for example by altering the affinity or rate of binding of a known activator to the target, by competing with the binding of a known activator to the target or by displacing a known activator bound to the target. Preferably, the inhibitor binds directly to Btk, thereby directly inhibiting its biological function or activity.

In accordance with the present invention, the inhibitor is an "inhibitor of Btk", i.e. the inhibitor reduces the biological function or activity of Btk. It is particularly preferred that the inhibitor specifically inhibits Btk, i.e. that it only inhibits the biological function or activity of Btk, but not the biological function or activity of other proteins.

Biological function or activity denotes in particular any known biological function or activity of Btk, including those elucidated in accordance with the present invention. Examples of said biological function or activity are the phosphorylation and activation of PLCγ2 in thrombocytes, thereby increasing cytosolic calcium levels and activating the effector molecule protein kinase C (PKC), which in turn result in the activation of platelets. All these functions or activities can be tested for either using any of a variety of standard methods known in the art, such as tyrosine phosphorylation of Btk or PLCγ2 or an increase of cytosolic Ca2+ concentration or on the basis of the teachings of the examples provided below, optionally in conjunction with molecular techniques such as phosphorylation assays or with the teachings of the documents cited therein.

In a preferred embodiment, the inhibitor reduces at least one, and preferably all of the above cited biological functions or activities of Btk by at least 50%, preferably by at least 75%, more preferred by at least 90% and even more preferred by at least 95% such as at least 98% or even by 100%. The term "reduction by at least" refers to a decreased biological function or activity such that Btk loses the recited amounts of one or more, preferably of all its biological functions or activities. For example, a reduction by at least 75% means that Btk loses 75% of its biological function or activity and, consequently, has only 25% of the biological function or activity remaining as compared to Btk that is not inhibited.

The function of any of the inhibitors referred to in the present invention may be identified and/or verified by using high throughput screening assays (HTS). High-throughput assays, independently of being biochemical, cellular or other assays, generally may be performed in wells of microtiter plates, wherein each plate may contain, for example 96, 384 or 1536 wells. Handling of the plates, including incubation at temperatures other than ambient temperature, and bringing into contact of test compounds with the assay mixture is preferably effected by one or more computer-controlled robotic systems including pipetting devices. In case large libraries of test compounds are to be screened and/or screening is to be effected within short time, mixtures of, for example 10, 20, 30, 40, 50 or 100 test compounds may be added to each well. In case a well exhibits biological activity, said mixture of test compounds may be de-convoluted to identify the one or more test compounds in said mixture giving rise to the observed biological activity.

The determination of binding of potential inhibitors can be effected in, for example, any binding assay, preferably biophysical binding assay, which may be used to identify binding of test molecules prior to performing the functional/activity assay with the inhibitor. Suitable biophysical binding assays are known in the art and comprise fluorescence polarization (FP) assay, fluorescence resonance energy transfer (FRET) assay and surface plasmon resonance (SPR) assay.

In cases where the inhibitor acts by decreasing the expression level of the target protein, the determination of the expression level of the protein can, for example, be carried out on the nucleic acid level or on the amino acid level. Methods for determining the expression of a protein on the nucleic acid level include, but are not limited to, northern blotting, PCR, RT-PCR or real RT-PCR. Methods for the determination of the expression of a protein on the amino acid level include, but are not limited to, western blotting or polyacrylamide gel electrophoresis in conjunction with protein staining techniques such as Coomassie Brilliant blue or silver-staining. These methods for the determination of the expression level of Btk on both the nucleic acid level as well as the amino acid level are well known in the art.

A number of Btk inhibitors are presently known and either approved for therapy or in clinical trials, and Btk selective irreversible small molecule inhibitors have been discovered (Pan Z. et al., *Chem Med Chem.* 2007; 2:58-61). For example, the small molecule inhibitor ibrutinib (PCI-32765) is a selective Btk inhibitor that has been approved by the FDA for the treatment of mantle cell lymphoma, the treatment of chronic lymphocytic leukemia and the treatment of Waldenström's macroglobulinemia, a form of non-Hodgkin's lymphoma (Byrd J C. et al., *N Engl J Med.* 2013; 369:32-42; Wang M L. et al., *N Engl J Med.* 2013; 369: 507-516). Further examples of Btk inhibitors currently in clinical trials include acalabrutinib (Phase 3) for relapsed CLL, GS-4059 or ONO/GS-4059 (previously ONO-4059; Phase 1), for Non-Hodgkin's Lymphoma and/or CLL, as well as spebrutinib (AVL-292, CC-292; Phase 1) and BGB-3111 (Phase 1) (Wu J et al *J Hematol Oncol* (2016) 9:80). Further reversible and irreversible Btk inhibitors, such as e.g. CNX-774, Imidazoquinoxaline, CGI1746, GDC-0834, RN486, have been described in the art and are summarised as Btk inhibitors that are in development for the treatment of rheumatoid arthritis in Whang and Chang, *Drug Discovery Today* 2014; 19:1200-1204; Other irreversible BTK inhibitors are BTKI-43607 and BTKI-43761 (Rigg R A, et al. *Am J Physiol Cell Physiol.* 2016; 310:C373-380).

It is particularly preferred in accordance with the present invention that the inhibitor is a thrombocyte-specific inhibitor. The inhibitor, in accordance with the present invention, may in certain embodiments be provided as a small molecule, a proteinaceous compound or as a nucleic acid molecule, such as e.g. an interfering or inhibiting nucleic acid molecule as described in more detail below. The inhibitor can also be encoded by a nucleic acid molecule, which can, for example, be incorporated into an expression vector comprising regulatory elements, such as megakaryocyte-specific promoters. For example, silencing of Btk in megakaryocytes and, subsequently, platelets can be achieved by using a simian or human immunodeficiency virus type 1-based, self-inactivating lentiviral vector harbouring a glycoprotein Iba promoter and an interfering or inhibiting nucleic acid molecule or a nucleic acid molecule encoding an e.g. proteinaceous inhibitor. Methods for targeted transfection of cells and suitable vectors are known in the art, see for example Sambrook and Russel ("Molecular Cloning, A Laboratory Manual", Cold Spring Harbor Laboratory, N.Y. (2001); Ohmori T. et al. *Arterioscler Thromb Vasc Biol.* 2007 October; 27(10):2266-72; Lavenu-Bombled C. et al. *Stem Cells.* 2007 June; 25(6):1571-7; Ohmori T. et al. *FASEB J.* 2006 July; 20(9):1522-4; Yasui K. et al. *Microbes Infect.* 2005 February; 7(2):240-7). Incorporation of the nucleic acid molecule encoding the inhibitor or directly affecting Btk transcription (siRNA, shRNA) into an expression vector enables the selective suppression of Btk expression in megakaryoyctes and platelets.

These inhibitors can be administered to the subject by any method available and suitable, including e.g. orally, intravenously, intradermally, subcutaneously, intramuscularly, intraperitoneally, topically (such as by powders, ointments, drops or transdermal patch), bucally, or as an oral or nasal spray. Oral administration is particularly preferred, especially when the inhibitor is ibrutinib.

The dosage regimen can be determined by the attending physician, based on clinical factors. As is well known in the medical arts, dosages for any one patient depends upon many factors, including the patient's size, body surface area, age, the particular compound to be administered, sex, time and route of administration, general health, and other drugs being administered concurrently. The effective amount for a given situation will readily be determined by routine experimentation and is within the skills and judgement of the ordinary clinician or physician. For example, if the inhibitor is the sole compound, the effective amount administered per dose can be in the range of about 70 to 140 mg per person, although, as noted above, this will be subject to therapeutic discretion. The particular amounts, as well as the corresponding adjustments in case more than one compound is to be administered, may be determined by conventional tests which are well known to the person skilled in the art. Administration may be once as a single dose or as repeat administrations. The interval time and amount of repeats required can be determined by the skilled person without further ado, preferably a dose of 140 mg is administered once every second day. Progress can be monitored by periodic assessment. The inhibitor of the invention may be administered locally or systemically. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like The term "arterial thrombosis" relates to thrombosis that develops in an artery, as opposed to venous thrombosis, which develops in a vein. Arterial thrombosis is generally caused by injury of a healthy artery, and the formation of a platelet- and fibrin-rich thrombus is essential for sealing the wall defect and stopping blood loss. In contrast the specific form of arterial thrombosis atherothrombosis is caused by the rupture of atherosclerotic plaques, or, less frequently, by erosion of the endothelium covering the atherosclerotic plaque. Thrombus formation is triggered by atherosclerotic plaque-derived thrombogenic substances that set in motion an avalanche of aggregating platelets and fibrin formation.

Atherosclerosis is a chronic disease of the arterial wall, and atherosclerotic plaques develop during a life-time as a consequence of continuous lipid deposition, inflammatory and fibrotic processes in the intima of the arterial wall. Whereas in healthy arteries the intima consists only of a thin inner layer of extracellular matrix, the intima of atherosclerotic plaques is drastically thickened. The plaques consist of lipids (largely oxidised), macrophages, smooth muscle cells, their necrotic, cell debris, calcium and extracellular matrix. Virchow coined the term "atheroma" for this material. Collagens of various types accumulate in atherosclerotic plaques and they differ structurally from collagens of healthy connective tissue (van Zanten, G. H. et al. *J Clin Invest* (1994), 93(2):615-32; Katsuda, S. and T. Kaji, *J Atheroscler Thromb* (2003). 10(5): 267-74; Penz et al. *FASEB Journal* 2005; 19(7):898-909). They also contain advanced glycation end products (Monnier V M et al *N Engl J Med* (1986), 314: 403-8; Sell et al *Arch Biochem Biophys* (2010), 493: 192-206) which may alter their platelet reactivity. The fundamentally different properties of atherosclerotic plaques compared to the intima of healthy arteries explain its different thrombogenicity: Atherosclerotic plaques are more thrombogenic than healthy arteries. Compared to normal arteries, platelet deposition onto human atherosclerotic coronary arteries is increased (van Zanten, G. H. et al. *J Clin Invest*. (1994), 93(2):615-32), and in mice the thrombotic response to injured carotid atherosclerotic arteries is much higher than to injured healthy carotid arteries (Hechler, B. and C. Gachet, *Thromb Haemost* (2011) 105 Suppl 1: S3-12).

The term "atherothrombosis" refers to an arterial thrombosis that develops as a consequence of the rupture of atheroma or after erosion of the endothelium covering the atherosclerotic plaque. In atherothrombosis erosion or rupture of vulnerable atherosclerotic plaques in coronary, extra- or intracranial (carotis or cerebral arteries, respectively) and peripheral (for example femoral) arteries exposes material that arrests circulating platelets and triggers thrombosis. The thrombus can occlude the artery, or the thrombus can detach, embolise and occlude the vessels (arteries, arterioles) downstream. Occlusion of the arterial circulation cuts blood supply to the tissue, and can cause ischemia and infarction of almost any organ in the body, dependent on the localisation of the thrombi or thrombo-emboli, most commonly acute coronary syndrome, myocardial infarction and ischemic stroke, but also peripheral arterial occlusive disease (PAOD).

Atherothrombosis, if not prevented by antiplatelet therapy, occurs also after percutaneous coronary intervention, and can accelerate neointima formation, restenosis and stent thrombosis.

In accordance with the present invention, it was found that an inhibitor of Btk, more specifically ibrutinib (PCI-32765), an orally applied irreversible Btk inhibitor, inhibited plaque and collagen-triggered platelet aggregation in blood under static conditions, both in vitro and ex vivo. In contrast, platelet aggregation stimulated by TRAP activating the PAR-1 receptor, ADP and ararchidonic acid (AA) was only modestly reduced by ibrutinib in vitro. Importantly, ibrutinib inhibited atherosclerotic plaque-induced platelet thrombus formation at arterial flow in two atherothrombosis models, i.e. in plaque homogenate and in plaque tissue sections exposed to arterially flowing blood.

Most importantly, the effects of ibrutinib, whether added to blood in vitro or studied in blood samples from patients on ibrutinib therapy, markedly differed between plaque- and collagen-stimulation of platelet aggregation under arterial flow conditions. Ibrutinib caused complete and plaque-selective platelet inhibition when blood was perfused over plaque material at shear rates typical for flow in intact coronary arteries (600/s; see FIGS. 2 and 5) or over mildly stenosing segments (1500/s; FIG. 3) of arteriosclerotic coronary arteries.

Figure 7:
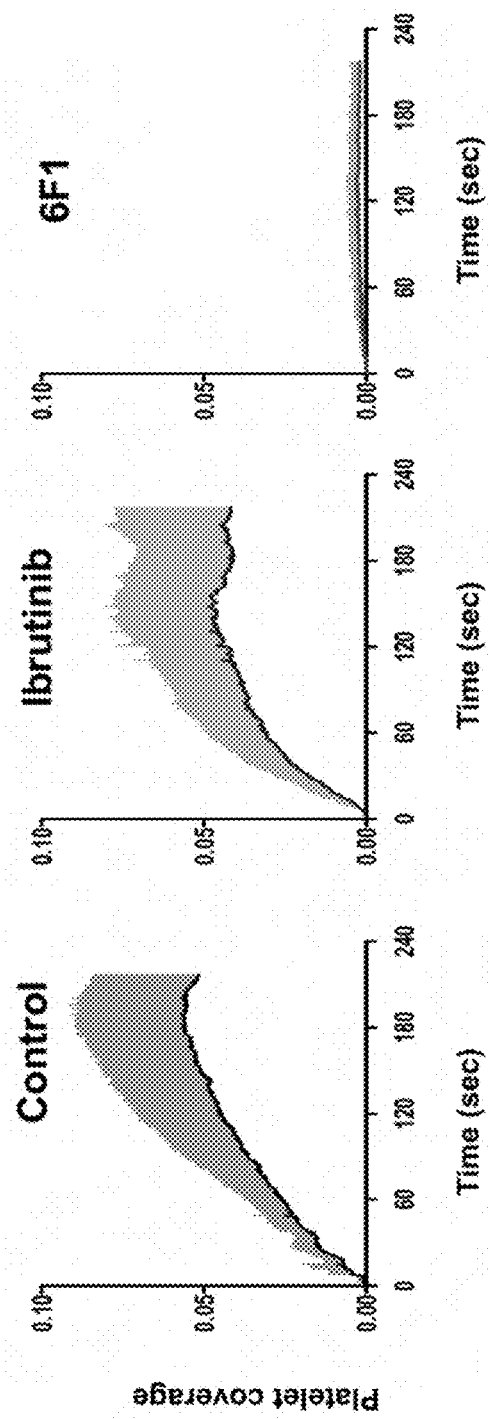

This difference between the effect on plaque- and collagen-stimulated platelet aggregation under arterial flow conditions might be explained with the observation that the platelet collagen receptor integrin $\alpha 2\beta 1$ plays an important role in platelet adhesion to collagen during arterial flow over isolated collagen fibres, which resembles the situation in healthy blood vessels, where integrin $\alpha 2\beta 1$ synergizes with GPVI in platelet aggregation to collagen. In contrast, platelet aggregation onto plaque under arterial flow exclusively depends on platelet GPVI but not on integrin $\alpha 2\beta 1$ (Penz et al. *FASEB Journal* 2005; 19(7):898-909; Schulz et al. *Basic Res Cardiol*. 2008; 103:356-367). In accordance ibrutinib did not inhibit integrin $\alpha_2\beta_1$-mediated platelet adhesion onto soluble type I collagen (FIG. 7). Thus, Btk does not signal downstream of integrin α2β1 and, thus, inhibition of Btk with ibrutinib selectively blocks platelet aggregation under flow dependent on GPVI-activation, but not platelet aggregation onto collagen under flow dependent on the combined activation of GPVI and integrin α2β1.

Figure 8:
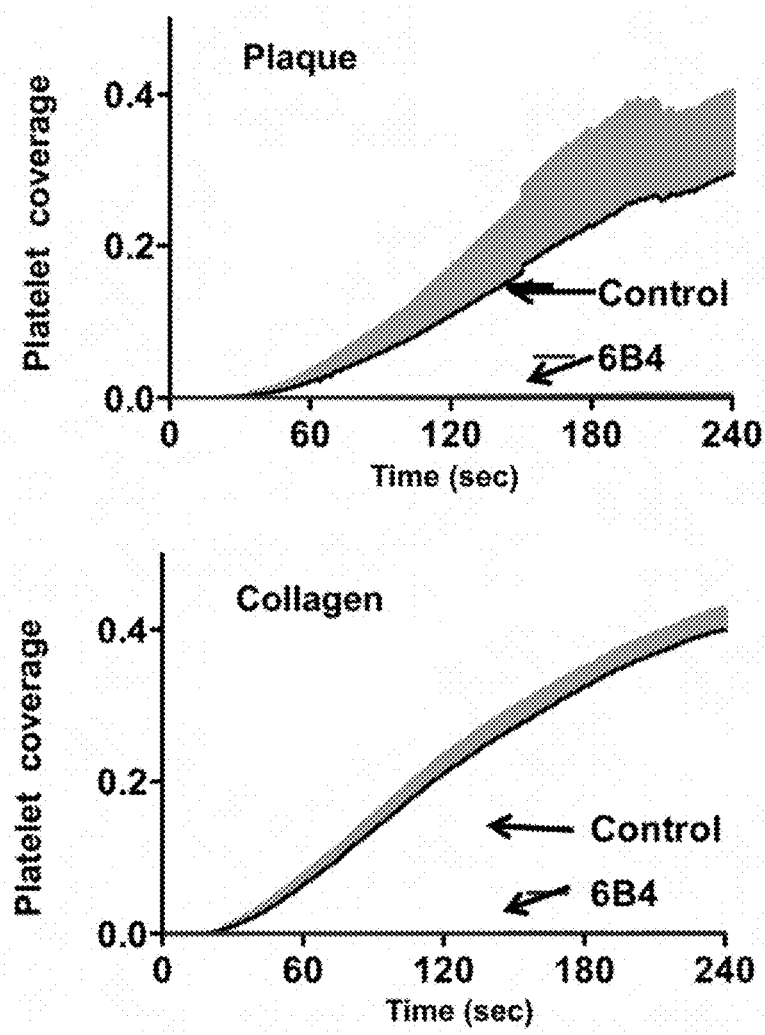

In addition to GPVI, Btk has been reported to also play a role in VWF/GPIb signaling. Collagen exposed after arterial wall injury or plaque rupture or erosion can first immobilize circulating VWF which in turn binds the platelet receptor GPIbα. This bridging by VWF is critically important to slow down circulating platelets, thereby enabling the growth of arterial thrombi at shear rates>1000/s. In the flow experiments shown in the appended examples (see e.g. Example 3) at a shear rate of 1500/s, ibrutinib had only a marginal, not-significant effect on collagen-induced platelet deposition, but it effectively inhibited plaque-induced platelet deposition (FIG. 3). Moreover, both plaque- and collagen-induced platelet aggregation at high shear arterial flow required the binding of VWF to GPIb. The antibody 6B4 which inhibits the interaction of GPIbα with VWF (Penz S M et al. *Thromb Haemost.* 2007; 97:435-443), inhibited both plaque homogenate- and collagen-induced platelet thrombus formation at this high shear rate equally (>95%) (FIG. 8). These results indicate that VWF activation of GPIb is required for both plaque- and collagen-induced platelet deposition at high shear arterial flow, but also implies that Btk-signaling downstream GPIb is not functionally relevant.

Further results in the appended examples show, that two new $2^{nd}$ generation oral irreversible inhibitors of Btk, which are more selective than ibrutinib, had similar effects as ibrutinib.

Figure 9:
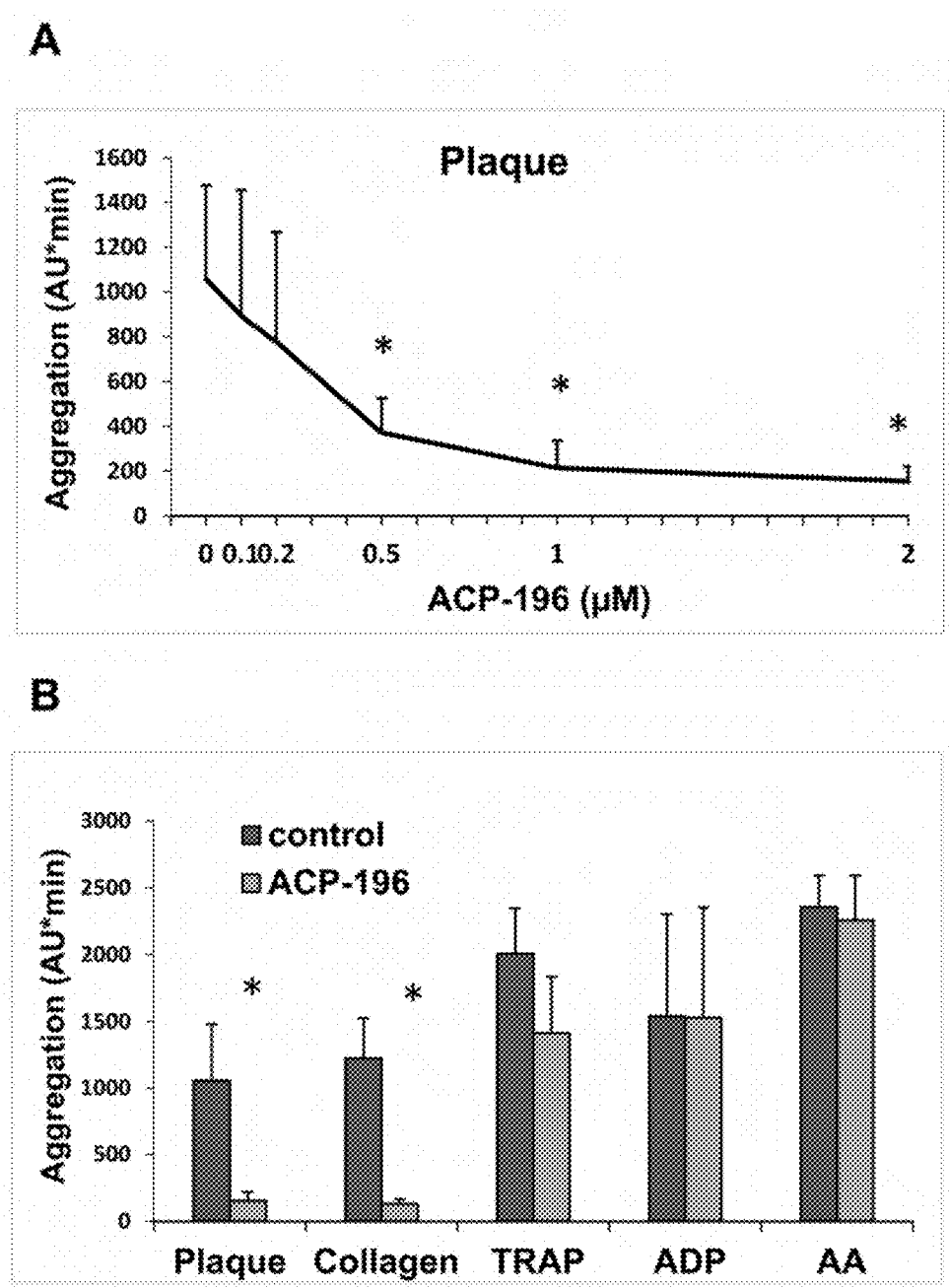
Figure 10:
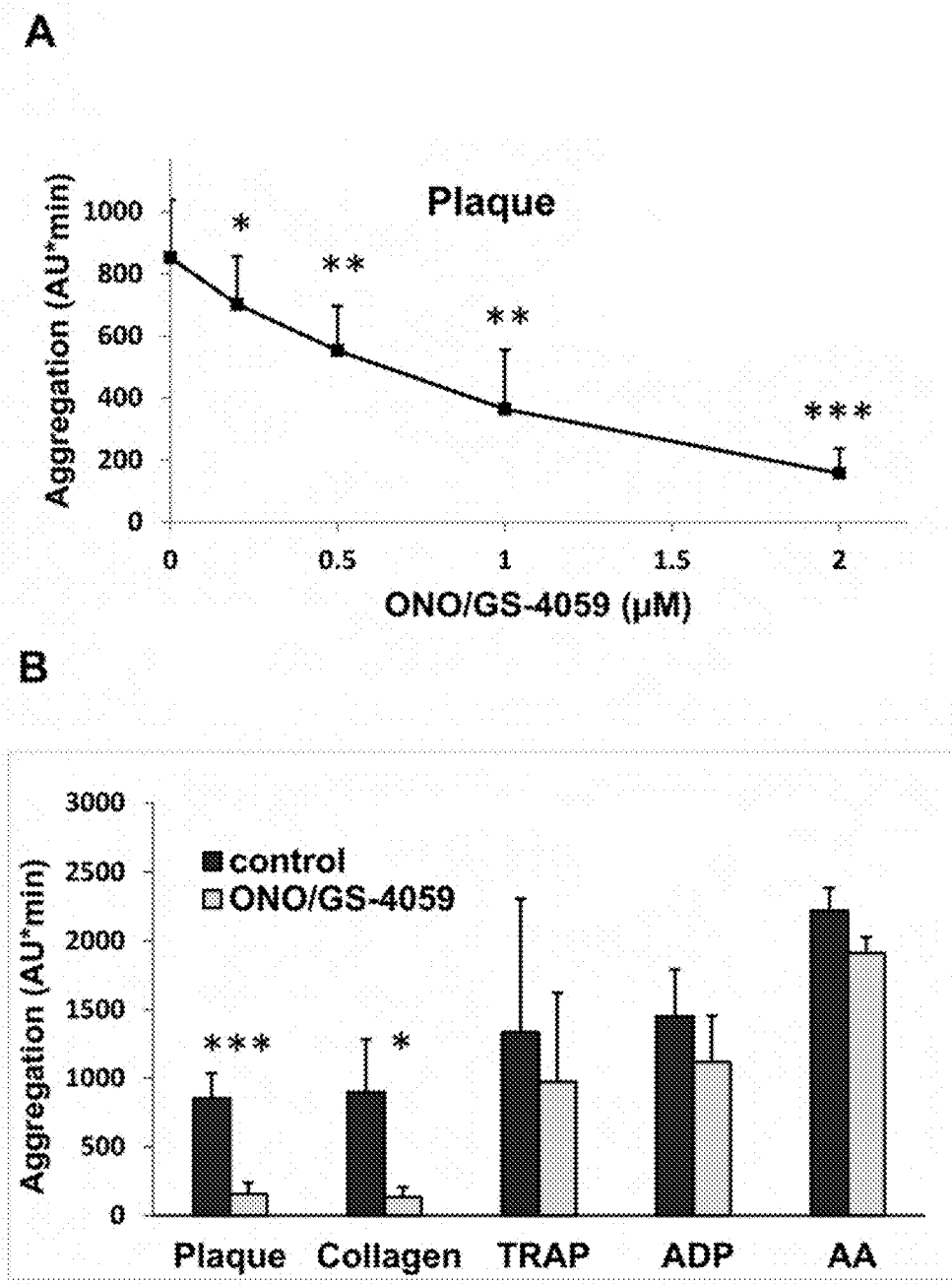
Figure 11:
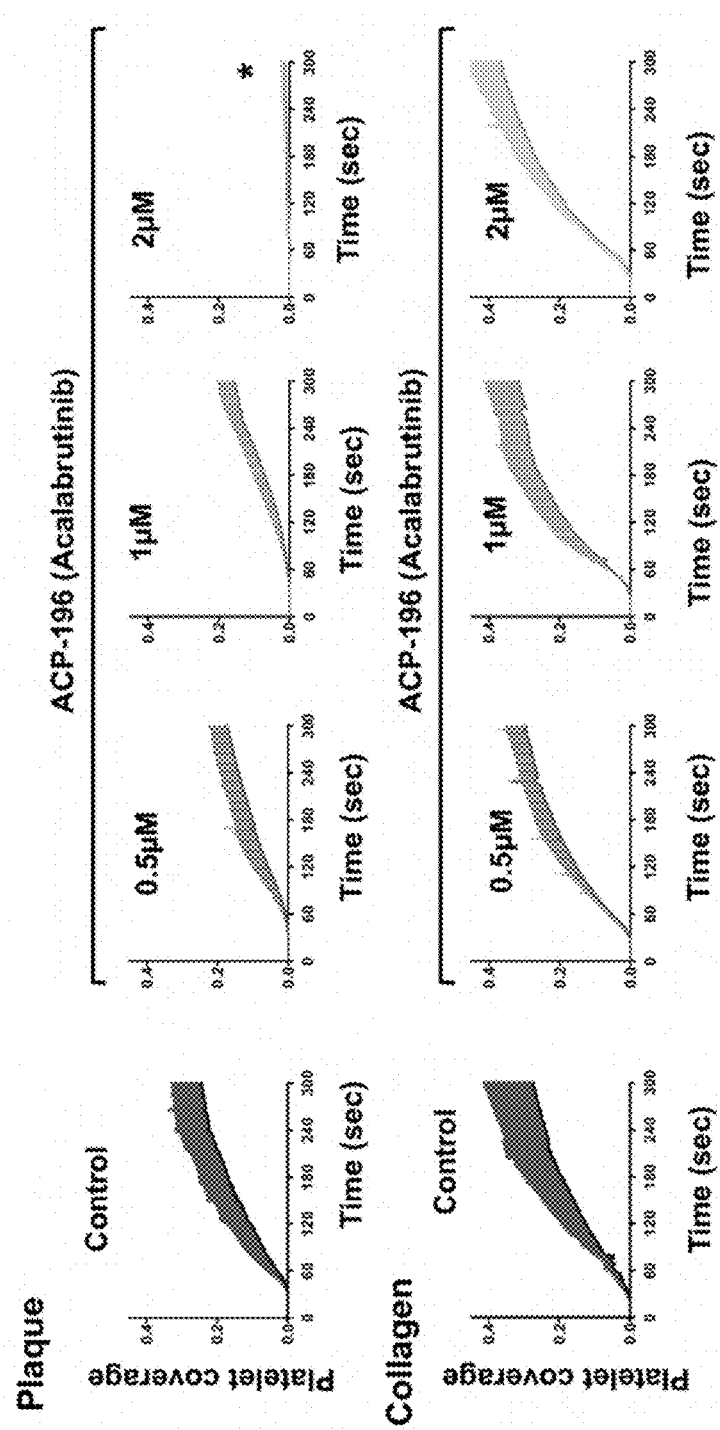
Figure 12:
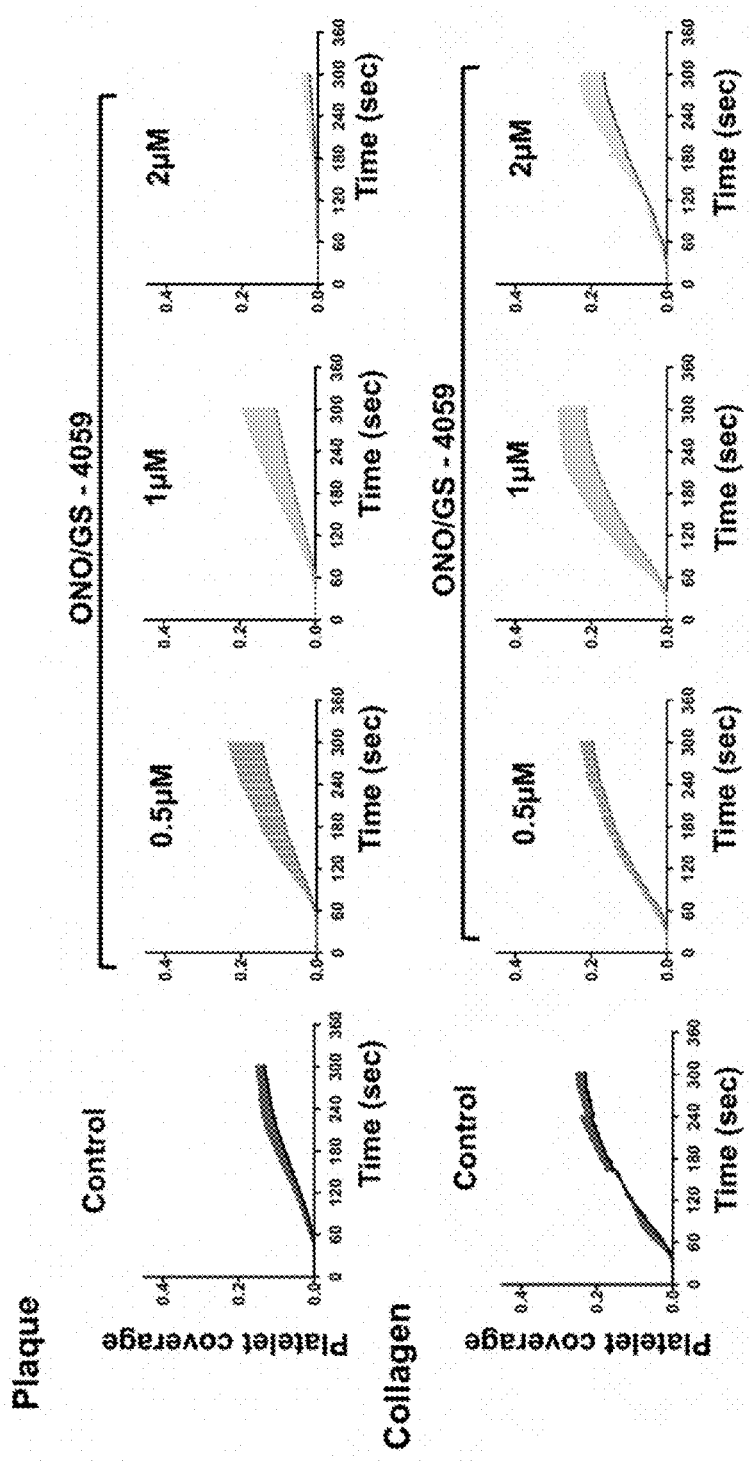
Figure 13:
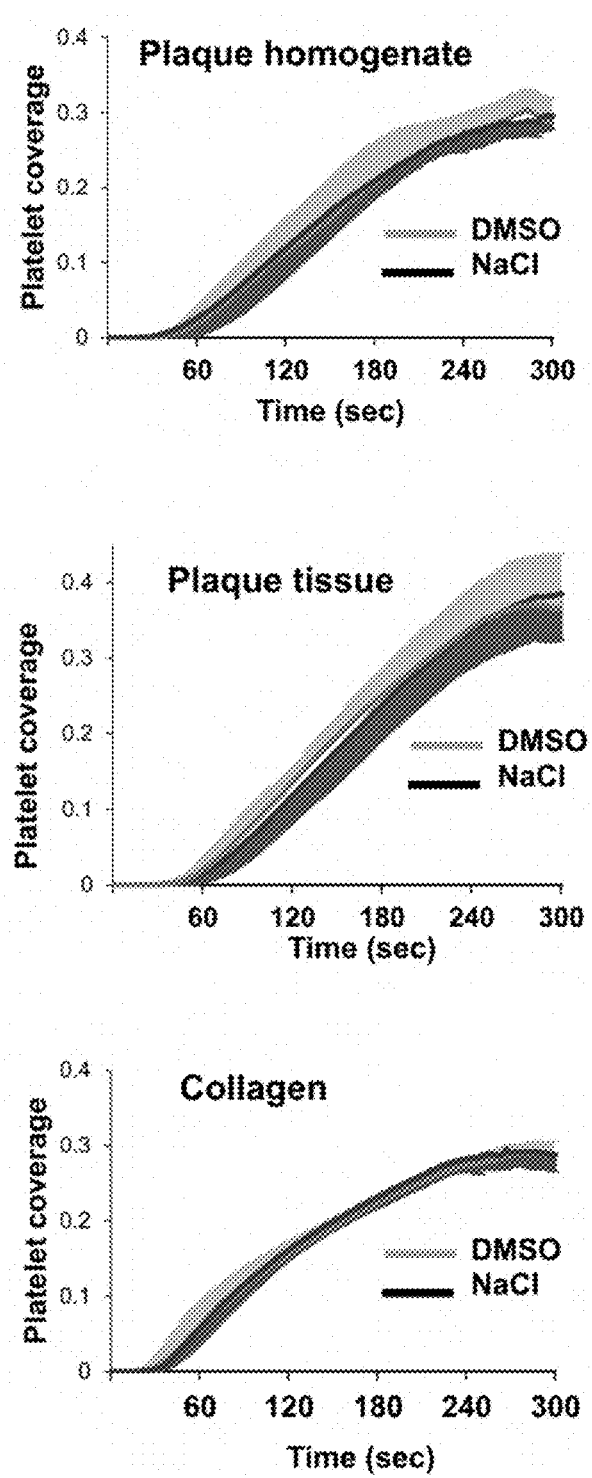

Acalabrutinib (ACP-196) and ONO/GS-4059 inhibited plaque and collagen-triggered platelet aggregation in blood under static conditions in vitro. In contrast, platelet aggregation stimulated by TRAP activating the PAR-1 receptor, ADP or AA was not or only marginally reduced by these inhibitors (FIGS. 9, 10). The IC50 value of acalabrutinib (ACP-196) for inhibition of plaque-induced platelet aggregation was around 0.4 µM, the IC50 of ONO/GS-4059 was around 1 µM (FIGS. 9A, 10A). Importantly, similar to ibrutinib, acalabrutinib (ACP-196) at 2 µM and ONO/GS-4059 at 2 µM caused effective and plaque-selective platelet inhibition, when blood was perfused over plaque material at arterial shear rate (FIGS. 11,12). DMSO (final concentration in blood 0.1%) used to dissolve the Btk-inhibitors did not affect the platelet response (FIG. 13).

Figure 14:
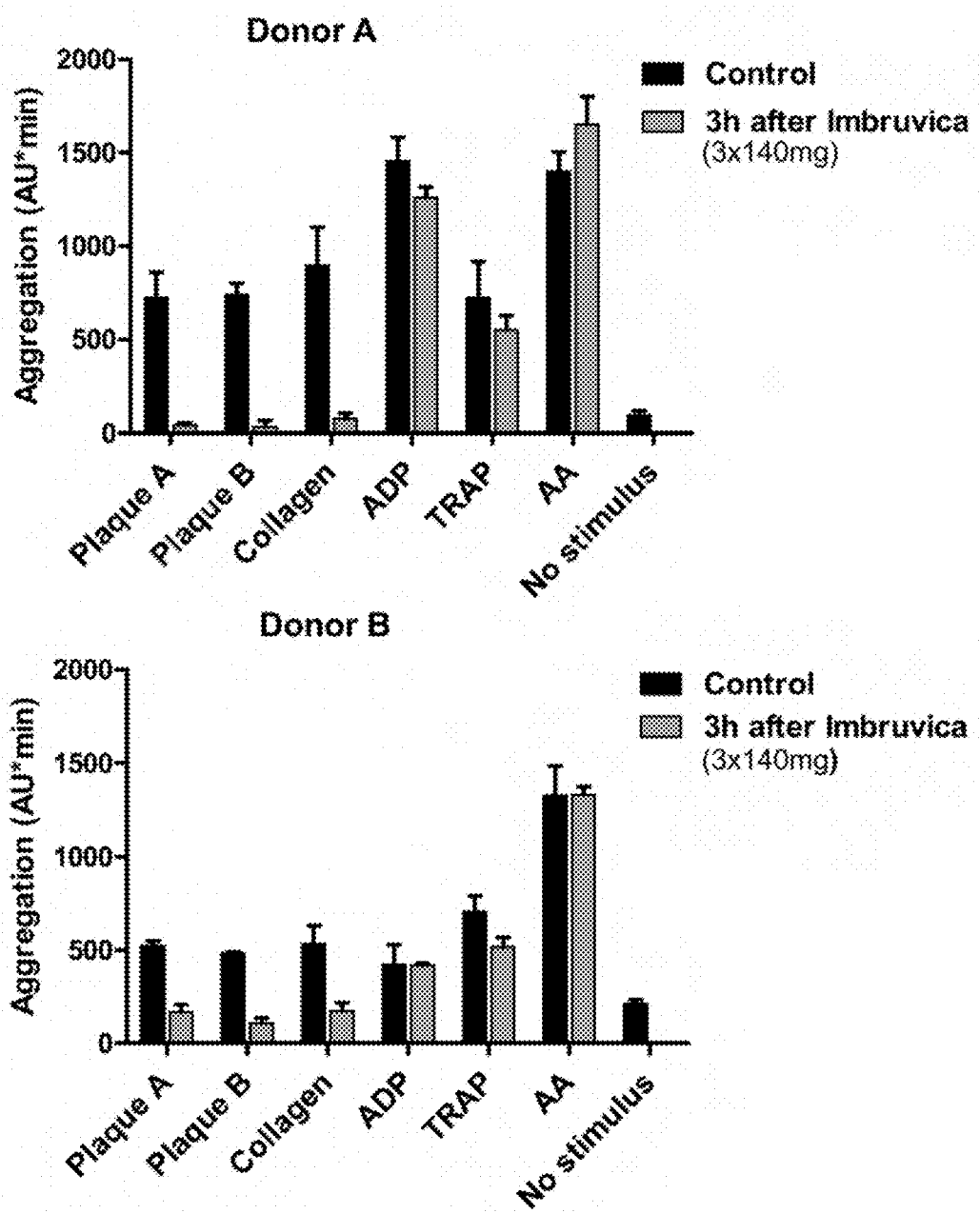
Figure 15:
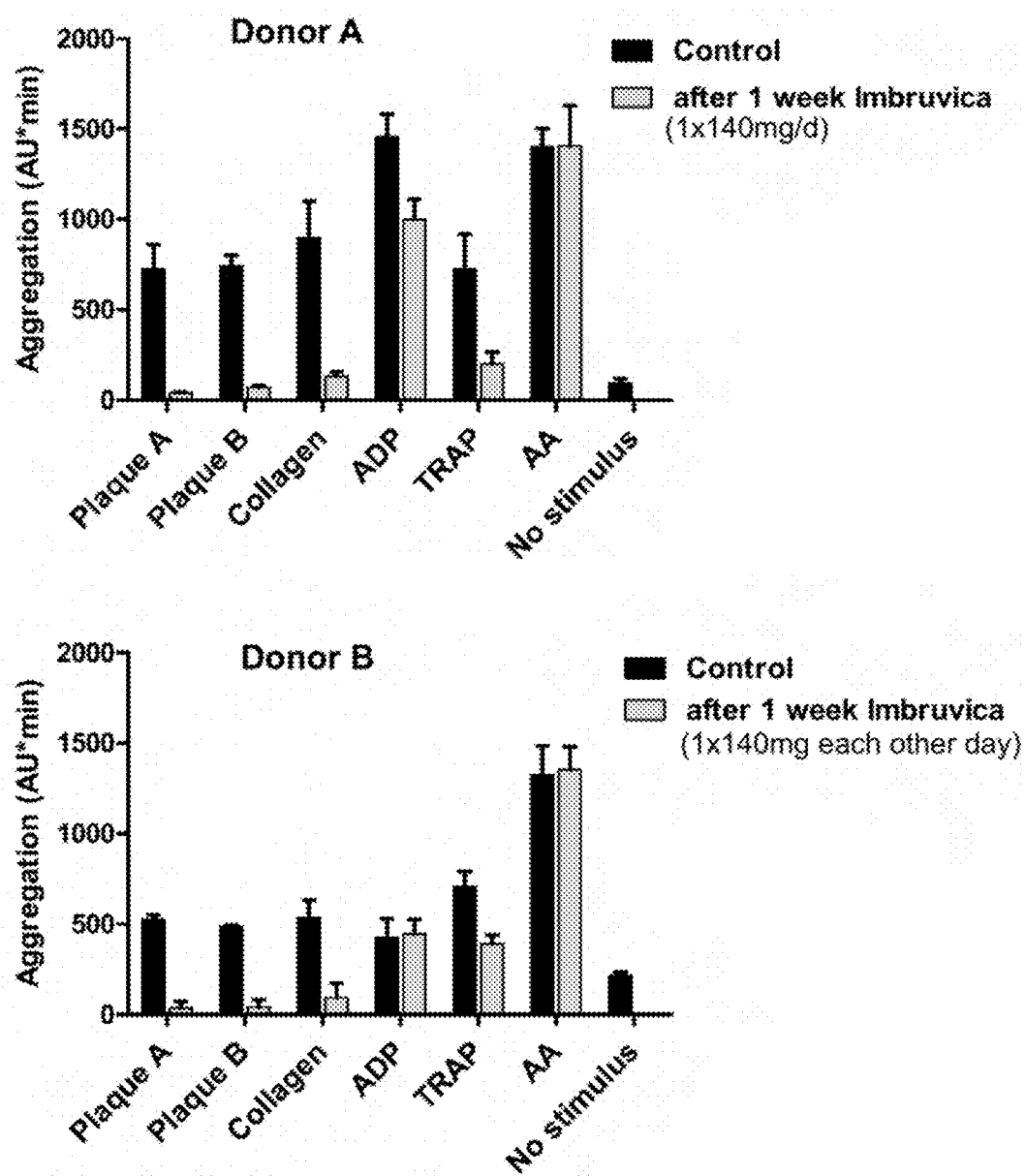
Figure 16:
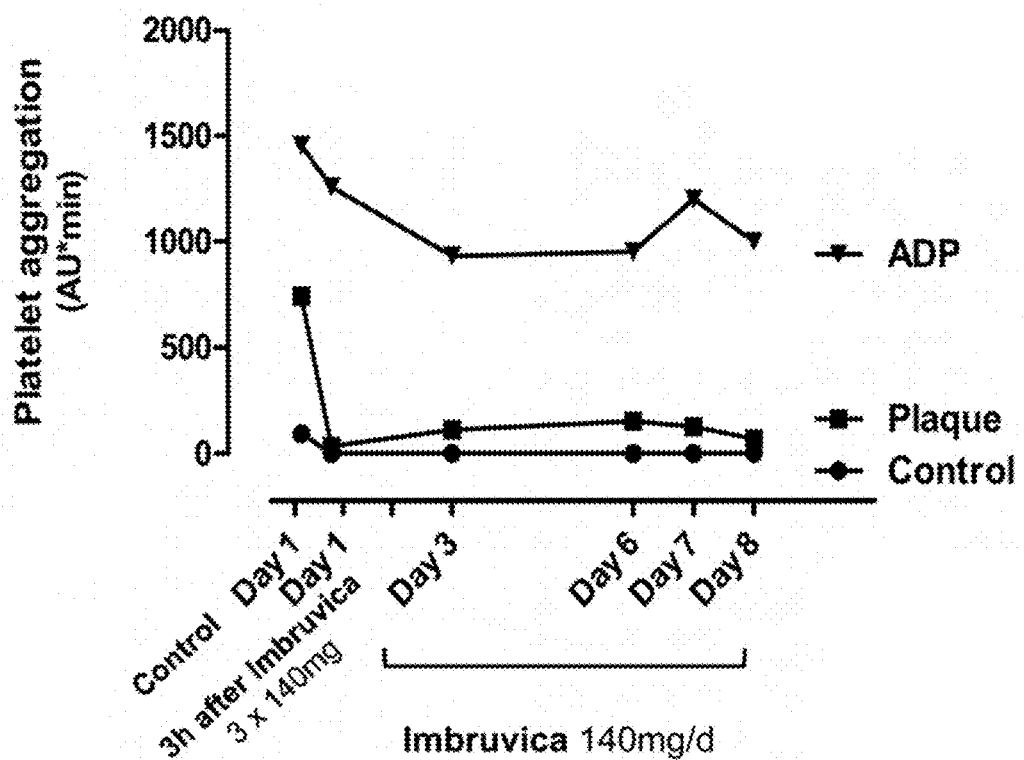
Figure 17A:
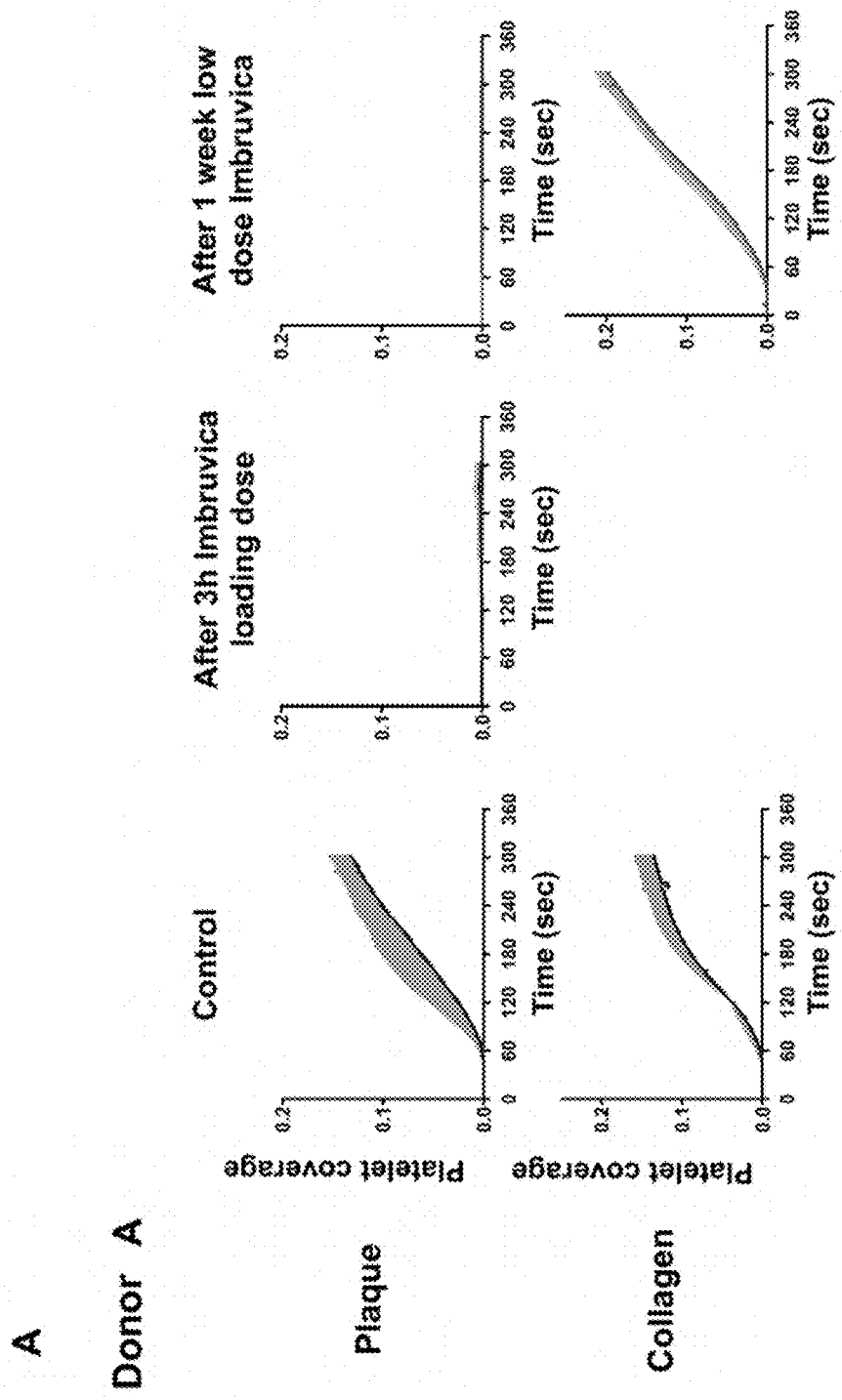

A pilot-study in two human volunteers showed that oral intake of low doses of ibrutinib (Imbruvica®) were sufficient to inhibit plaque-induced platelet aggregation under static and flow conditions. Plaque- and collagen-induced platelet aggregation were completely inhibited 3 h after oral intake of a loading dose of 3×140 mg Imbruvica® (FIG. 14). Inhibition of plaque-induced aggregation was maintained by oral intake of either Imbruvica® 140 mg each day or 140 mg each other day for 1 week (FIGS. 15, 16). These low ibrutinib doses were also sufficient to inhibit platelet adhesion and aggregation onto atherosclerotic plaques but not onto collagen under arterial flow (FIG. 17A, B).

Ibrutinib, acalabrutinib (ACP-196) and ONO/GS-4059 suppressed plaque-triggered platelet thrombus formation much more potently than previously observed with aspirin plus P2Y12 receptor antagonists (Penz S M et al. *Thromb Haemost.* 2007; 97:435-443; Jamasbi J. et al. *J Am Coll Cardiol.* 2015; 65:2404-2415), the established dual antiplatelet therapy.

The results shown in the appended examples indicate that targeting Btk can prevent atherothrombosis; in particular it can prevent occluding acute atherothrombosis more effectively and more selectively, because, as also shown in the appended examples, it leaves physiologic platelet activation in haemostasis largely intact.

This latter finding of intact physiologic platelet activation in haemostasis is particularly surprising. Although it was previously found that patients with Btk-deficiency, such as e.g. patients with X-linked agammaglobulinemia (XLA), do not show spontaneous bleeding or haemorrhage (Stewart D M. et al. *Current allergy and asthma reports.* 2001; 1:558-565; Futatani T. et al. *Br J Haematol* 2001; 114:141-149), the use of Btk-inhibitors, such as ibrutinib, was shown to be associated with disturbed vWF- and collagen-stimulated platelet activation (Levade M. et al. *Blood.* 2014; 124:3991-3995; Kamel S. et al. *Leukemia.* 2015; 29:783-787). Low grade bleeding tendency, including spontaneous bruising, epistaxis or petechiae, is frequently observed in ibrutinib-treated patients (Wang M L. et al. *Blood.* 2015; 126:739-745. 2015; Shatzel J J et al. *J Thromb Haemostas* (2017) 15: 1-13). Interestingly, treatment of patients with new, more selective BTK inhibitors (such as ACP-196, ONO/GS-4059, and BGB-3111) apparently causes less bleeding than ibrutinib (Byrd J C et al *N Engl J Med* (2016) 374; 4: 323-332; Wu J et al *J Hematol Oncol* (2016) 9:80; Walter H S et al *Blood* (2017) 129(20):2808-2810). Also the new Btk inhibitors BTKI-43607 and BTKI-43761 did not show an increase of template skin bleeding time or an effect on coagulation non-human primates (Rigg R A, et al. *Am J Physiol Cell Physiol.* 2016; 310:C373-380).

Overall, the data presented herein show that the use of Btk inhibitors holds promise to be more efficient and safer than standard dual platelet therapy with aspirin and P2Y12 antagonists, and also circumvents the drawbacks of an antibody based intervention, such as potentially encountered when using anti-GPVI-antibodies.

The present invention further relates to a method of treating and/or preventing atherothrombosis comprising administering a pharmaceutically effective amount of an inhibitor of Bruton's tyrosine kinase (Btk) to a subject in need thereof.

All definitions and preferred embodiments provided herein with regard to the inhibitor of the invention apply mutatis mutandis to this method of the invention, unless specifically detailed otherwise.

In a preferred embodiment of the inhibitor or the method of the invention, the inhibitor is a small molecule, an antibody or antibody mimetic, an aptamer, a siRNA, a shRNA, a miRNA, a ribozyme, or an antisense nucleic acid molecule.

The "small molecule" as used herein is preferably an organic molecule. Organic molecules relate or belong to the class of chemical compounds having a carbon basis, the carbon atoms linked together by carbon-carbon bonds. The original definition of the term organic related to the source of chemical compounds, with organic compounds being those carbon-containing compounds obtained from plant or animal or microbial sources, whereas inorganic compounds were obtained from mineral sources. Organic compounds can be natural or synthetic. The organic molecule is preferably an aromatic molecule and more preferably a heteroaromatic molecule. In organic chemistry, the term aromaticity is used to describe a cyclic (ring-shaped), planar (flat) molecule with a ring of resonance bonds that exhibits more stability than other geometric or connective arrangements with the same set of atoms. Aromatic molecules are very stable, and do not break apart easily to react with other substances. In a heteroaromatic molecule at least one of the atoms in the aromatic ring is an atom other than carbon, e.g. N, S, or O.

The heteroaromatic molecule is preferably a molecule comprising an azole motif (i.e. azole, di-azole, tri-azole or a tetra-azole motif) and/or an azine motif (i.e. azine, di-azine, or tri-azine motif). The heteroaromatic molecule is more preferably a molecule comprising a pyridine (azine), pyrimidine (diazine), triazine, azine, pyrazole or imidiazole motif. The heteroaromatic molecule is even more preferably a molecule comprising a pyrimidine (diazine), pyrazole or imidiazole motif. For all above-described organic molecules the molecular weight is preferably in the range of 150 Da to 1500 Da and more preferably in the range of 300 Da to 1000 Da.

Alternatively, the "small molecule" in accordance with the present invention may be an inorganic compound. Inorganic compounds are derived from mineral sources and include all compounds without carbon atoms (except carbon dioxide, carbon monoxide and carbonates). Preferably, the small molecule has a molecular weight of less than about 2000 amu, or less than about 1000 amu such as less than about 500 amu, and even more preferably less than about 250 amu. The size of a small molecule can be determined by methods well-known in the art, e.g., mass spectrometry. The small molecules may be designed, for example, based on the crystal structure of the target molecule, where sites presumably responsible for the biological activity, can be identified and verified in in vivo assays such as in vivo high-throughput screening (HTS) assays. Non-limiting examples of a small molecule inhibitor of Btk is ibrutinib (also known as PCI-32765), acalabrutinib (ACP-196), and ONO/GS-4059 which have been employed in the examples provided herein below. Other examples, such as BTKI-43607 and BTKI-43761, have also been described to inhibit Btk irreversibly in platelets (Rigg R A. et al. *Am J Physiol Cell Physiol.* 2016; 310:C373-380). Further small molecule inhibitors of Btk such as spebrutinib (AVL-292, CC-292), BGB-3111, CNX-774, Imidazoquinoxaline, CGI1746, GDC-0834, RN486, and HM-71224 have been described in the art and are inter alfa summarised in Wank and Chang, *Drug Discovery Today* 2014; 19:1200-1204, and by Wu J et al *J Hematol Oncol* (2016) 9:80). The following Table 1 shows the structural formulas of the small molecule inhibitors of Btk ibrutinib, acalabrutinib (ACP-196), ONO/GS-4059, BGB-3111, CC-292, BMS-986142, CNX-774, Imidazoquinoxaline, CGI1746, GDC-0834, RN486, and HM-71224, Other Btk-inhibitors are BTKI-43607 and BTKI-43761, whose structures have not been disclosed (Rigg R A. et al. *Am J Physiol Cell Physiol.* 2016; 310:C373-380).

TABLE 1

| Inhibitor designation | Structure |
|---|---|
| ibrutinib | 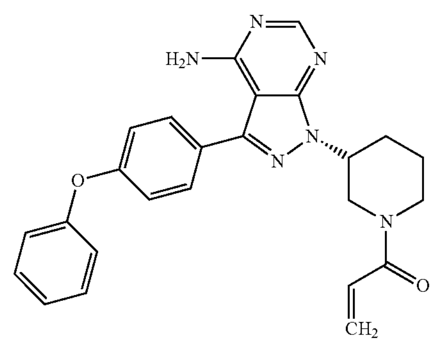 |
| acalabrutinib (ACP-196) | 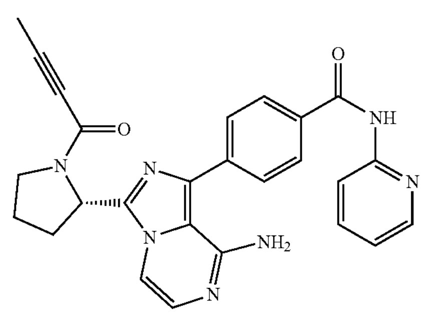 [SMILES: CC#CC(=O)N1CCC[C@H]1c1nc(-c2ccc(C(=O)Nc3ccccn3)cc2)c2c(N)nccn12] |
| ONO/GS-4059 | 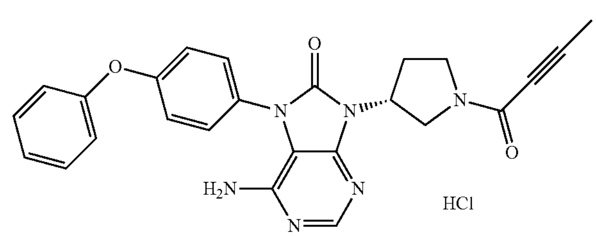 [SMILES: CC#CC(=O)N1CC[C@@H](n2c(=O)n(-c3ccc(Oc4ccccc4)cc3)c3c(N)ncnc32)C1 ; Cl] |

TABLE 1-continued
| Inhibitor designation | Structure |
|---|---|
| BGB-3111 | 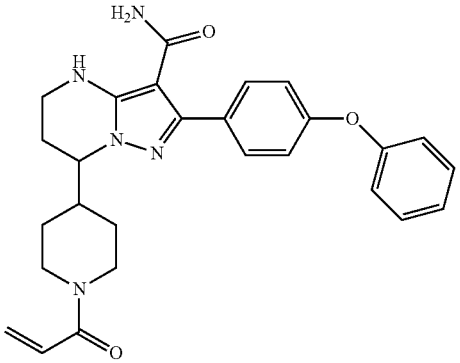 [SMILES: C=CC(=O)N1CCC(C2CCNc3c(C(N)=O)c(-c4ccc(Oc5ccccc5)cc4)nn32)CC1] |
| spebrutinib (CC-292, AVL-292) | 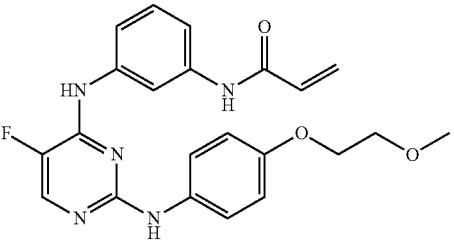 [SMILES: C=CC(=O)Nc1cccc(Nc2nc(Nc3ccc(OCCOC)cc3)ncc2F)c1] |
| BMS-986142 | 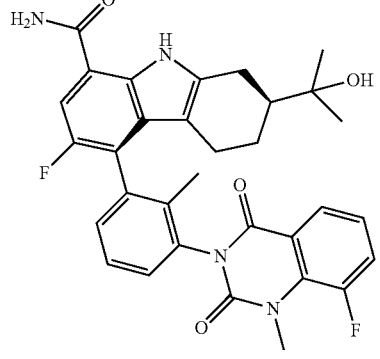 |
| CNX-774 | 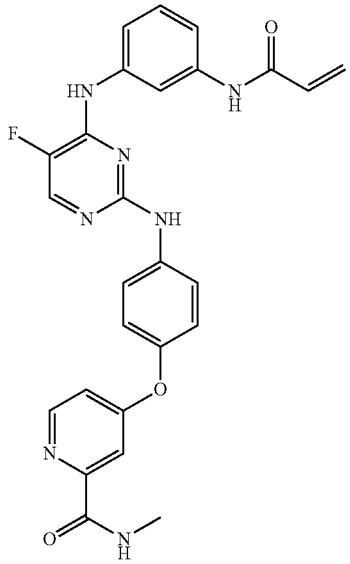 [SMILES: C=CC(=O)Nc1cccc(Nc2nc(Nc3ccc(Oc4ccnc(C(=O)NC)c4)cc3)ncc2F)c1] |

TABLE 1-continued

| Inhibitor designation | Structure |
|---|---|
| Imidazoquinoxaline (Compound 36) | 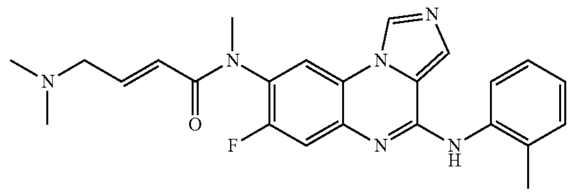 [SMILES: Cc1ccccc1Nc1nc2cc(F)c(N(C)C(=O)/C=C/CN(C)C)cc2n2cncc12] |
| CGI1746 | 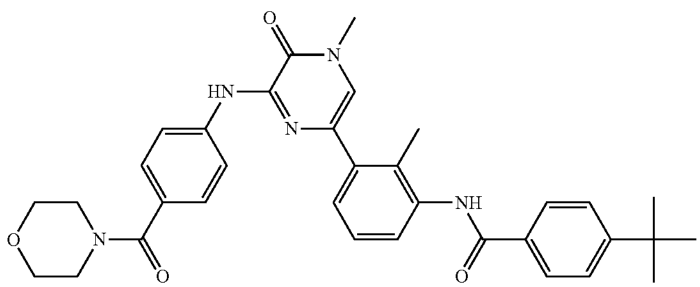 [SMILES: Cc1c(NC(=O)c2ccc(C(C)(C)C)cc2)cccc1-c1cn(C)c(=O)c(Nc2ccc(C(=O)N3CCOCC3)cc2)n1] |
| GDC-0834 | 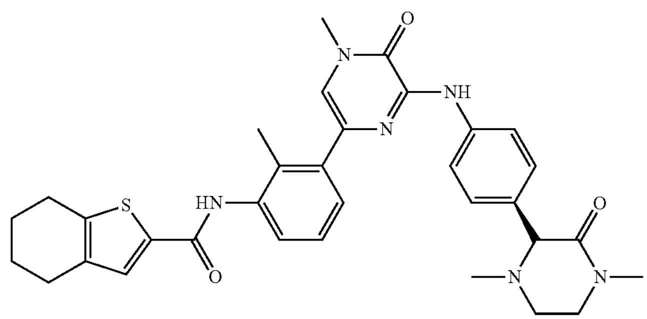 |
| HM-71224 | 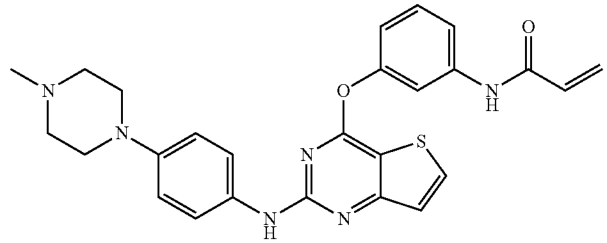 [SMILES: C=CC(=O)Nc1cccc(Oc2nc(Nc3ccc(N4CCN(C)CC4)cc3)nc3ccsc23)c1] |
| RN486 | 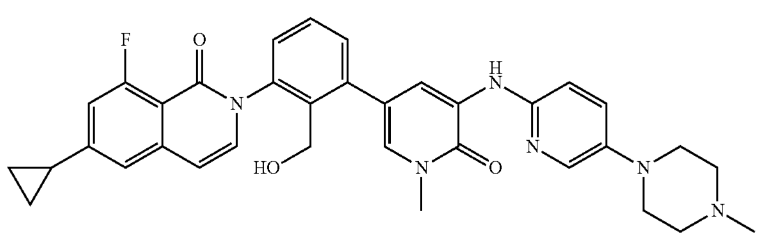 |

The term "antibody" as used in accordance with the present invention comprises, for example, polyclonal or monoclonal antibodies. Furthermore, also derivatives or fragments thereof, which still retain the binding specificity to the target, e.g. Btk, are comprised in the term "antibody". Antibody fragments or derivatives comprise, inter alia, Fab or Fab' fragments, Fd, F(ab')$_2$, Fv or scFv fragments, single domain $V_H$ or V-like domains, such as VhH or V-NAR-domains, as well as multimeric formats such as minibodies, diabodies, tribodies or triplebodies, tetrabodies or chemically conjugated Fab'-multimers (see, for example, Harlow and Lane "Antibodies, A Laboratory Manual", Cold Spring Harbor Laboratory Press, 198; Harlow and Lane "Using Antibodies: A Laboratory Manual" Cold Spring Harbor Laboratory Press, 1999; Altshuler E P, Serebryanaya D V, Katrukha A G. 2010, Biochemistry (Mosc)., vol. 75(13), 1584; Holliger P, Hudson P J. 2005, Nat Biotechnol., vol. 23(9), 1126).

The term "antibody" also includes embodiments such as chimeric (human constant domain, non-human variable domain), single chain and humanised (human antibody with the exception of non-human CDRs) antibodies.

Various techniques for the production of antibodies are well known in the art and described, e.g. in Harlow and Lane (1988) and (1999) and Altshuler et al., 2010, loc. cit. Thus, polyclonal antibodies can be obtained from the blood of an animal following immunisation with an antigen in mixture with additives and adjuvants and monoclonal antibodies can be produced by any technique which provides antibodies produced by continuous cell line cultures. Examples for such techniques are described, e.g. in Harlow E and Lane D, Cold Spring Harbor Laboratory Press, 1988; Harlow E and Lane D, Using Antibodies: A Laboratory Manual, Cold Spring Harbor Laboratory Press, 1999 and include the hybridoma technique originally described by Köhler and Milstein, 1975, the trioma technique, the human B-cell hybridoma technique (see e.g. Kozbor D, 1983, Immunology Today, vol. 4, 7; Li J, et al. 2006, PNAS, vol. 103(10), 3557) and the EBV-hybridoma technique to produce human monoclonal antibodies (Cole et al., 1985, Alan R. Liss, Inc, 77-96). Furthermore, recombinant antibodies may be obtained from monoclonal antibodies or can be prepared de novo using various display methods such as phage, ribosomal, mRNA, or cell display. A suitable system for the expression of the recombinant (humanised) antibodies may be selected from, for example, bacteria, yeast, insects, mammalian cell lines or transgenic animals or plants (see, e.g., U.S. Pat. No. 6,080,560; Holliger P, Hudson P J. 2005, Nat Biotechnol., vol. 23(9), 11265). Further, techniques described for the production of single chain antibodies (see, inter alia, U.S. Pat. No. 4,946,778) can be adapted to produce single chain antibodies specific for an epitope of Btk. Surface plasmon resonance as employed in the BIAcore system can be used to increase the efficiency of phage antibodies.

As used herein, the term "antibody mimetics" refers to compounds which, like antibodies, can specifically bind antigens, such as Btk in the present case, but which are not structurally related to antibodies. Antibody mimetics are usually artificial peptides or proteins with a molar mass of about 3 to 20 kDa. For example, an antibody mimetic may be selected from the group consisting of affibodies, adnectins, anticalins, DARPins, avimers, nanofitins, affilins, Kunitz domain peptides and Fynomers®. These polypeptides are well known in the art and are described in further detail herein below.

The term "affibody", as used herein, refers to a family of antibody mimetics which is derived from the Z-domain of staphylococcal protein A. Structurally, affibody molecules are based on a three-helix bundle domain which can also be incorporated into fusion proteins. In itself, an affibody has a molecular mass of around 6 kDa and is stable at high temperatures and under acidic or alkaline conditions. Target specificity, i.e. against Btk, is obtained by randomisation of 13 amino acids located in two alpha-helices involved in the binding activity of the parent protein domain (Feldwisch J, Tolmachev V.; (2012) Methods Mol Biol. 899:103-26).

The term "adnectin" (also referred to as "monobody"), as used herein, relates to a molecule based on the 10th extracellular domain of human fibronectin III (10Fn3), which adopts an Ig-like β-sandwich fold of 94 residues with 2 to 3 exposed loops, but lacks the central disulphide bridge (Gebauer and Skerra (2009) Curr Opinion in Chemical Biology 13:245-255). Adnectins with the desired target specificity, i.e. against Btk, can be genetically engineered by introducing modifications in specific loops of the protein.

The term "anticalin", as used herein, refers to an engineered protein derived from a lipocalin (Beste G, Schmidt F S, Stibora T, Skerra A. (1999) Proc Natl Acad Sci USA. 96(5)1898-903; Gebauer and Skerra (2009) Curr Opinion in Chemical Biology 13:245-255). Anticalins possess an eight-stranded β-barrel which forms a highly conserved core unit among the lipocalins and naturally forms binding sites for ligands by means of four structurally variable loops at the open end. Anticalins, although not homologous to the IgG superfamily, show features that so far have been considered typical for the binding sites of antibodies: (i) high structural plasticity as a consequence of sequence variation and (ii) elevated conformational flexibility, allowing induced fit to targets with differing shape.

As used herein, the term "DARPin" refers to a designed ankyrin repeat domain (166 residues), which provides a rigid interface arising from typically three repeated β-turns. DARPins usually carry three repeats corresponding to an artificial consensus sequence, wherein six positions per repeat are randomised. Consequently, DARPins lack structural flexibility (Gebauer and Skerra, 2009).

The term "avimer", as used herein, refers to a class of antibody mimetics which consist of two or more peptide sequences of 30 to 35 amino acids each, which are derived from A-domains of various membrane receptors and which are connected by linker peptides. Binding of target molecules occurs via the A-domain and domains with the desired binding specificity, i.e. for Btk, can be selected, for example, by phage display techniques. The binding specificity of the different A-domains contained in an avimer may, but does not have to be identical (Weidle U H, et al., (2013), Cancer Genomics Proteomics; 10(4):155-68).

A "nanofitin" (also known as affitin) is an antibody mimetic protein that is derived from the DNA binding protein Sac7d of *Sulfolobus acidocaldarius*. Nanofitins usually have a molecular weight of around 7 kDa and are designed to specifically bind a target molecule, such as e.g. Btk, by randomising the amino acids on the binding surface (Mouratou B, Behar G, Paillard-Laurance L, Colinet S, Pecorari F., (2012) Methods Mol Biol.; 805:315-31).

The term "affilin", as used herein, refers to antibody mimetics that are developed by using either gamma-B crystalline or ubiquitin as a scaffold and modifying amino-acids on the surface of these proteins by random mutagenesis. Selection of affilins with the desired target specificity, i.e. against Btk, is effected, for example, by phage display or ribosome display techniques. Depending on the scaffold, affilins have a molecular weight of approximately 10 or 20 kDa. As used herein, the term affilin also refers to di- or multimerised forms of affilins (Weidle U H, et al., (2013), Cancer Genomics Proteomics; 10(4):155-68).

A "Kunitz domain peptide" is derived from the Kunitz domain of a Kunitz-type protease inhibitor such as bovine pancreatic trypsin inhibitor (BPTI), amyloid precursor protein (APP) or tissue factor pathway inhibitor (TFPI). Kunitz domains have a molecular weight of approximately 6 kDA and domains with the required target specificity, i.e. against Btk, can be selected by display techniques such as phage display (Weidle et al., (2013), Cancer Genomics Proteomics; 10(4):155-68).

As used herein, the term "Fynomer®" refers to a non-immunoglobulin-derived binding polypeptide derived from the human Fyn SH3 domain. Fyn SH3-derived polypeptides are well-known in the art and have been described e.g. in Grabulovski et al. (2007) JBC, 282, p. 3196-3204, WO 2008/022759, Bertschinger et al (2007) Protein Eng Des Sel 20(2):57-68, Gebauer and Skerra (2009) Curr Opinion in Chemical Biology 13:245-255, or Schlatter et al. (2012), MAbs 4:4, 1-12).

Aptamers are nucleic acid molecules or peptide molecules that bind a specific target molecule. Aptamers are usually created by selecting them from a large random sequence pool, but natural aptamers also exist in riboswitches. Aptamers can be used for both basic research and clinical purposes as macromolecular drugs. Aptamers can be combined with ribozymes to self-cleave in the presence of their target molecule. These compound molecules have additional research, industrial and clinical applications (Osborne et. al. (1997), Current Opinion in Chemical Biology, 1:5-9; Stull & Szoka (1995), Pharmaceutical Research, 12, 4:465-483).

Nucleic acid aptamers are nucleic acid species that normally consist of (usually short) strands of oligonucleotides. Typically, they have been engineered through repeated rounds of in vitro selection or equivalently, SELEX (systematic evolution of ligands by exponential enrichment) to bind to various molecular targets such as small molecules, proteins, nucleic acids, and even cells, tissues and organisms.

Peptide aptamers are usually peptides or proteins that are designed to interfere with other protein interactions inside cells. They consist of a variable peptide loop attached at both ends to a protein scaffold. This double structural constraint greatly increases the binding affinity of the peptide aptamer to levels comparable to an antibody's (nanomolar range). The variable peptide loop typically comprises 10 to 20 amino acids, and the scaffold may be any protein having good solubility properties. Currently, the bacterial protein Thioredoxin-A is the most commonly used scaffold protein, the variable peptide loop being inserted within the redox-active site, which is a -Cys-Gly-Pro-Cys- loop in the wild protein, the two cysteines lateral chains being able to form a disulfide bridge. Peptide aptamer selection can be made using different systems, but the most widely used is currently the yeast two-hybrid system.

Aptamers offer the utility for biotechnological and therapeutic applications as they offer molecular recognition properties that rival those of the commonly used biomolecules, in particular antibodies. In addition to their discriminatory recognition, aptamers offer advantages over antibodies as they can be engineered completely in a test tube, are readily produced by chemical synthesis, possess desirable storage properties, and elicit little or no immunogenicity in therapeutic applications. Non-modified aptamers are cleared rapidly from the bloodstream, with a half-life of minutes to hours, mainly due to nuclease degradation and clearance from the body by the kidneys, a result of the aptamers' inherently low molecular weight. Unmodified aptamer applications currently focus on treating transient conditions such as blood clotting, or treating organs such as the eye where local delivery is possible. This rapid clearance can be an advantage in applications such as in vivo diagnostic imaging. Several modifications, such as 2'-fluorine-substituted pyrimidines, polyethylene glycol (PEG) linkage, fusion to albumin or other half life extending proteins etc. are available to scientists such that the half-life of aptamers can be increased for several days or even weeks.

The term "peptide" as used herein describes a group of molecules consisting of up to 30 amino acids, whereas the term "polypeptide" (also referred to as "protein") as used herein describes a group of molecules consisting of more than 30 amino acids. The group of peptides and polypeptides are referred to together by using the term "(poly)peptide".

In accordance with the present invention, the term "small interfering RNA (siRNA)", also known as short interfering RNA or silencing RNA, refers to a class of 18 to 30, preferably 19 to 25, most preferred 21 to 23 or even more preferably 21 nucleotide-long double-stranded RNA molecules that play a variety of roles in biology. Most notably, siRNA is involved in the RNA interference (RNAi) pathway where the siRNA interferes with the expression of a specific gene. In addition to their role in the RNAi pathway, siRNAs also act in RNAi-related pathways, e.g. as an antiviral mechanism or in shaping the chromatin structure of a genome.

siRNAs naturally found in nature have a well defined structure: a short double-strand of RNA (dsRNA) with 2-nt 3' overhangs on either end. Each strand has a 5' phosphate group and a 3' hydroxyl (—OH) group. This structure is the result of processing by dicer, an enzyme that converts either long dsRNAs or small hairpin RNAs into siRNAs. siRNAs can also be exogenously (artificially) introduced into cells to bring about the specific knockdown of a gene of interest. Essentially any gene for which the sequence is known can thus be targeted based on sequence complementarity with an appropriately tailored siRNA. The double-stranded RNA molecule or a metabolic processing product thereof is capable of mediating target-specific nucleic acid modifications, particularly RNA interference and/or DNA methylation. Exogenously introduced siRNAs may be devoid of overhangs at their 3' and 5' ends, however, it is preferred that at least one RNA strand has a 5'- and/or 3'-overhang. Preferably, one end of the double-strand has a 3'-overhang from 1 to 5 nucleotides, more preferably from 1 to 3 nucleotides and most preferably 2 nucleotides. The other end may be blunt-ended or has up to 6 nucleotides 3'-overhang. In general, any RNA molecule suitable to act as siRNA is envisioned in the present invention. The most efficient silencing was so far obtained with siRNA duplexes composed of 21-nt sense and 21-nt antisense strands, paired in a manner to have a 2-nt 3'-overhang. The sequence of the 2-nt 3' overhang makes a small contribution to the specificity of target recognition restricted to the unpaired nucleotide adjacent to the first base pair (Elbashir et al. 2001). 2'-deoxynucleotides in the 3' overhangs are as efficient as ribonucleotides, but are often cheaper to synthesize and probably more nuclease resistant. Delivery of siRNA may be accomplished using any of the methods known in the art, for example by combining the siRNA with saline and administering the combination intravenously or intranasally or by formulating siRNA in glucose (such as for example 5% glucose) or cationic lipids and polymers can be used for siRNA delivery in vivo through systemic routes either intravenously (IV) or intraperitoneally (IP) (Fougerolles et al. (2008), Current Opinion in Pharmacology, 8:280-285; Lu et al. (2008), Methods in Molecular Biology, vol. 437: Drug Delivery Systems—Chapter 3: Delivering Small Interfering RNA for Novel Therapeutics).

A short hairpin RNA (shRNA) is a sequence of RNA that makes a tight hairpin turn that can be used to silence gene expression via RNA interference. shRNA uses a vector introduced into cells and utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs which match the siRNA that is bound to it. si/shRNAs to be used in the present invention are preferably chemically synthesized using appropriately protected ribonucleoside phosphoramidites and a conventional DNA/RNA synthesizer. Suppliers of RNA synthesis reagents are Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). Most conveniently, siRNAs or shRNAs are obtained from commercial RNA oligo synthesis suppliers, which sell RNA-synthesis products of different quality and costs. In general, the RNAs applicable in the present invention are conventionally synthesized and are readily provided in a quality suitable for RNAi.

Further molecules effecting RNAi include, for example, microRNAs (miRNA). Said RNA species are single-stranded RNA molecules. Endogenously present miRNA molecules regulate gene expression by binding to a complementary mRNA transcript and triggering of the degradation of said mRNA transcript through a process similar to RNA interference. Accordingly, exogenous miRNA may be employed as an inhibitor of Btk after introduction into the respective cells.

A ribozyme (from ribonucleic acid enzyme, also called RNA enzyme or catalytic RNA) is an RNA molecule that catalyses a chemical reaction. Many natural ribozymes catalyse either their own cleavage or the cleavage of other RNAs, but they have also been found to catalyse the aminotransferase activity of the ribosome. Non-limiting examples of well-characterised small self-cleaving RNAs are the hammerhead, hairpin, hepatitis delta virus, and in vitro-selected lead-dependent ribozymes, whereas the group I intron is an example for larger ribozymes. The principle of catalytic self-cleavage has become well established in recent years. The hammerhead ribozymes are characterised best among the RNA molecules with ribozyme activity. Since it was shown that hammerhead structures can be integrated into heterologous RNA sequences and that ribozyme activity can thereby be transferred to these molecules, it appears that catalytic antisense sequences for almost any target sequence can be created, provided the target sequence contains a potential matching cleavage site. The basic principle of constructing hammerhead ribozymes is as follows: A region of interest of the RNA, which contains the GUC (or CUC) triplet, is selected. Two oligonucleotide strands, each usually with 6 to 8 nucleotides, are taken and the catalytic hammerhead sequence is inserted between them. The best results are usually obtained with short ribozymes and target sequences.

A recent development, also useful in accordance with the present invention, is the combination of an aptamer, recognizing a small compound, with a hammerhead ribozyme. The conformational change induced in the aptamer upon binding the target molecule can regulate the catalytic function of the ribozyme.

The term "antisense nucleic acid molecule", as used herein, refers to a nucleic acid which is complementary to a target nucleic acid. An antisense molecule in accordance with the invention is capable of interacting with the target nucleic acid, more specifically it is capable of hybridizing with the target nucleic acid. Due to the formation of the hybrid, transcription of the target gene(s) and/or translation of the target mRNA is reduced or blocked. Standard methods relating to antisense technology have been described (see, e.g., Melani et al., Cancer Res. (1991) 51:2897-2901).

In a further preferred embodiment of the inhibitor or the method of the invention, the inhibitor binds irreversibly to Btk.

"Irreversible binding", in accordance with the present invention, refers to binding of the inhibitor to Btk in such a manner that the two molecules remain bound until Btk or the cell containing said Btk molecule ceases to exist, e.g. due to degradation of Btk or cell death of the respective cell. Methods to determine whether a Btk inhibitor binds irreversibly to Btk are well known and include, without being limiting, testing whether an inhibitor binds covalently to the cysteine 481 (Cys-481) in the active domain of Btk, for example by tagging the inhibitor with a fluorophore such as Bodipy-FL, incubating it with cell lysates and detecting fluorescent Btk by fluorescence scanning after gel electrophoretic protein separation, as described e.g. in Honigberg et al, PNAS 2010.

In a more preferred embodiment of the inhibitor or the method of the invention, the inhibitor is ibrutinib or an analogue thereof.

Ibrutinib, also known as PCI-32765 and marketed under the name Imbruvica, has the IUPAC name 1-[(3R)-3-[4-Amino-3-(4-phenoxyphenyl)-1H-pyrazolo[3,4-d]pyrimidin-1-yl]piperidin-1-yl]prop-2-en-1-one. It binds covalently to a cysteine residue (Cys-481) in the active site, thereby potently and irreversibly inhibiting Btk (Honigberg L A. et al., *Proc Natl Acad Sci USA.* 2010; 107:13075-13080). Ibrutinib can be commercially obtained from Selleckchem (Houston, USA).

In accordance with the present invention, the inhibitor can also be an analogue of ibrutinib. Such analogues include functional as well as structural analogues of ibrutinib. Further examples of Btk inhibitors include acalabrutinib (ACP-196), ONO/GS-4059 spebrutinib (AVL-292, CC-292), and BGB-3111 (Wu J et al *J Hematol Oncol* (2016) 9:80). Further reversible and irreversible Btk inhibitors, such as e.g. CNX-774, Imidazoquinoxaline, CGI1746, GDC-0834, RN486, have been described in the art and are summarised as Btk inhibitors that are in development for the treatment of rheumatoid arthritis in Whang and Chang, *Drug Discovery Today* 2014; 19:1200-1204). Other irreversible BTK inhibitors are BTKI-43607 and BTKI-43761 as being analogs of ibrutinib that form a covalent bond with a cysteine residue on Btk (Rigg R A, et al. *Am J Physiol Cell Physiol.* 2016; 310:C373-380). Functional analogues of ibrutinib include, without being limiting, Btk inhibitors that covalently bind the cysteine residue at position 481 in the active site of the kinase domain, such as e.g. the irreversible inhibitors CC-292, CNX-774, and Imidazoquinoxaline, all of which have been described in the art and are summarised in Whang and Chang, *Drug Discovery Today* 2014; 19:1200-1204.

In accordance with a more preferred embodiment of the inhibitor or the method of the invention, the inhibitor (said inhibitor preferably being ibrutinib, acalabrutinib (ACP-196), ONO/GS-4059, BGB-3111, or an analogue thereof) is used/administered at a dosage of 10 to 140 mg per day or 20 to 280 mg each other day. This dosage is preferably preceded by a loading dose of once 250-560 mg.

Within the list of ibrutinib, acalabrutinib (ACP-196), ONO/GS-4059, BGB-3111, and an analogue thereof ibrutinib, acalabrutinib (ACP-196), ONO/GS-4059, and an analogue thereof are preferably used/administered as the inhibitor. Preferred dosages of ibrutinib to be used are low drug doses of 35 to 140 mg per day (preferably 70 to 140 mg per day), or 70 to 140 mg each other day. Preferred dosages of acalabrutinib to be used are low drug doses twice 10 to 50 mg per day, so that the total daily dose is 20 to 100 mg. Dosages of ONO/GS-4059 to be used are are preferably low drug doses of 20 to 100 mg per day and 50 to 100 mg each other day. Preferred dosages of BGB-3111 to be used are low drug doses of twice 20 to 80 mg per day, so that the total daily dose is 40 to 160 mg.

By employing such low dosages of ibrutinib, acalabrutinib, ONO/GS-4059, BGB-3111, or an analogue thereof a selective inhibition of Btk mainly in platelets, if not only in platelets, can be achieved. Such low dosages ensure that ibrutinib, ibrutinib, acalabrutinib, ONO/GS-4059, BGB-3111, or an analogue thereof covalently inactivates Btk in platelets passing through the portal circulation during the absorption phase. This approach exploits the lack of de novo enzyme synthesis in platelets, and allows for the suppression of the key mechanism for plaque-initiated thrombus formation in platelets for their life span, but does not inhibit Btk in other cells.

It is preferred that before one of the above-described low dosages of ibrutinib, acalabrutinib, ONO/GS-4059, BGB-3111, or an analogue thereof is used/administered, an initial loading dose is used/administered. The loading dose is higher than the above-described low dosages and is to ensure an immediate effect on the platelets in the patient to be treated.

In accordance with an even more preferred embodiment of the inhibitor or the method of the invention, the inhibitor is used/administered at a loading dose of 280 to 560 mg, and a maintenance dosage of 10 to 140 mg per day or 40 to 280 mg each other day.

Preferred loading doses (which are taken once) for ibrutinib are 280 to 560 mg, for acalabrutinib 200 to 300 mg, for ONO/GS-4059 320 to 480 mg, and for BGB-3111 320 to 480 mg.

In a further preferred embodiment of the inhibitor or the method of the invention, the inhibitor is comprised in a pharmaceutical composition, optionally further comprising a pharmaceutically acceptable carrier, excipient and/or diluent.

The term "pharmaceutical composition", as used herein, relates to a composition for administration to a patient, preferably a human patient. The pharmaceutical composition of the invention comprises at least one, such as at least two, e.g. at least three, in further embodiments at least four such as at last five of the above mentioned inhibitors. In cases where more than one inhibitor is comprised in the pharmaceutical composition it is understood that none of these inhibitors has any essentially inhibitory effect on the other inhibitors also comprised in the composition.

The composition may be in solid, liquid or gaseous form and may be, inter alia, in a form of (a) powder(s), (a) tablet(s), (a) solution(s) or (an) aerosol(s).

It is preferred that said pharmaceutical composition comprises a pharmaceutically acceptable carrier, excipient and/or diluent. Examples of suitable pharmaceutical carriers, excipients and/or diluents are well known in the art and include phosphate buffered saline solutions, water, emulsions, such as oil/water emulsions, various types of wetting agents, lubricants, binding agents, fillers, sterile solutions etc.

Compositions comprising such carriers can be formulated by well known conventional methods. These pharmaceutical compositions can be administered to the subject at a suitable dose. The dosage regimen will be determined by the attending physician and clinical factors. All definitions and preferred embodiments provided herein above with regard to the administration of the inhibitor of the invention, such as routes of administration, preferred dosages as well as means of determining same, apply mutatis mutandis to the administration of the pharmaceutical composition of the present invention.

It is particularly preferred that said pharmaceutical composition comprises further agents known in the art to antagonize arterial thrombosis. Since the pharmaceutical preparation of the present invention relies on the inhibitors referred to herein, it is preferred that those mentioned further agents are only used as a supplement, i.e. at a reduced dose as compared to the recommended dose when used as the only drug, so as to e.g. reduce side effects conferred by the further agents.

Unless otherwise defined, all technical and scientific terms used herein have the same meaning as commonly understood by one of ordinary skill in the art to which this invention belongs. In case of conflict, the patent specification, including definitions, will prevail.

Regarding the embodiments characterised in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The above considerations apply mutatis mutandis to all appended claims. To give a non-limiting example, the combination of claims 7, 6 and 4 is clearly and unambiguously envisaged in view of the claim structure. The same applies for example to the combination of claims 7, 6 and 5, etc.

The figures show:

FIG. 1: Ibrutinib inhibits static platelet aggregation stimulated by plaque and collagen but not TRAP and ADP. Blood samples were pre-incubated for 15 minutes with solvent (DMSO, 0.1%) or ibrutinib (1 µM) before stimulation with plaque (833 µg/ml), collagen (0.1-0.3 µg/ml), TRAP (5 µM), ADP (5 µM), AA (0.6 mM) or without stimulation. (A) Representative MEA tracings. The numbers in the tracings indicate cumulative aggregation values (AU*min) measured at 10 minutes. (B) Dose-response curve of ibrutinib on inhibition of plaque-induced platelet aggregation. (C) Dose-response curve of ibrutinib on inhibition of collagen-induced platelet aggregation. (D) Effect of ibrutinib (1 µM) on plaque-, collagen-, TRAP-, ADP-induced platelet aggregation and spontaneous platelet aggregation. Values are mean±SD (n=5).

Figure 2:
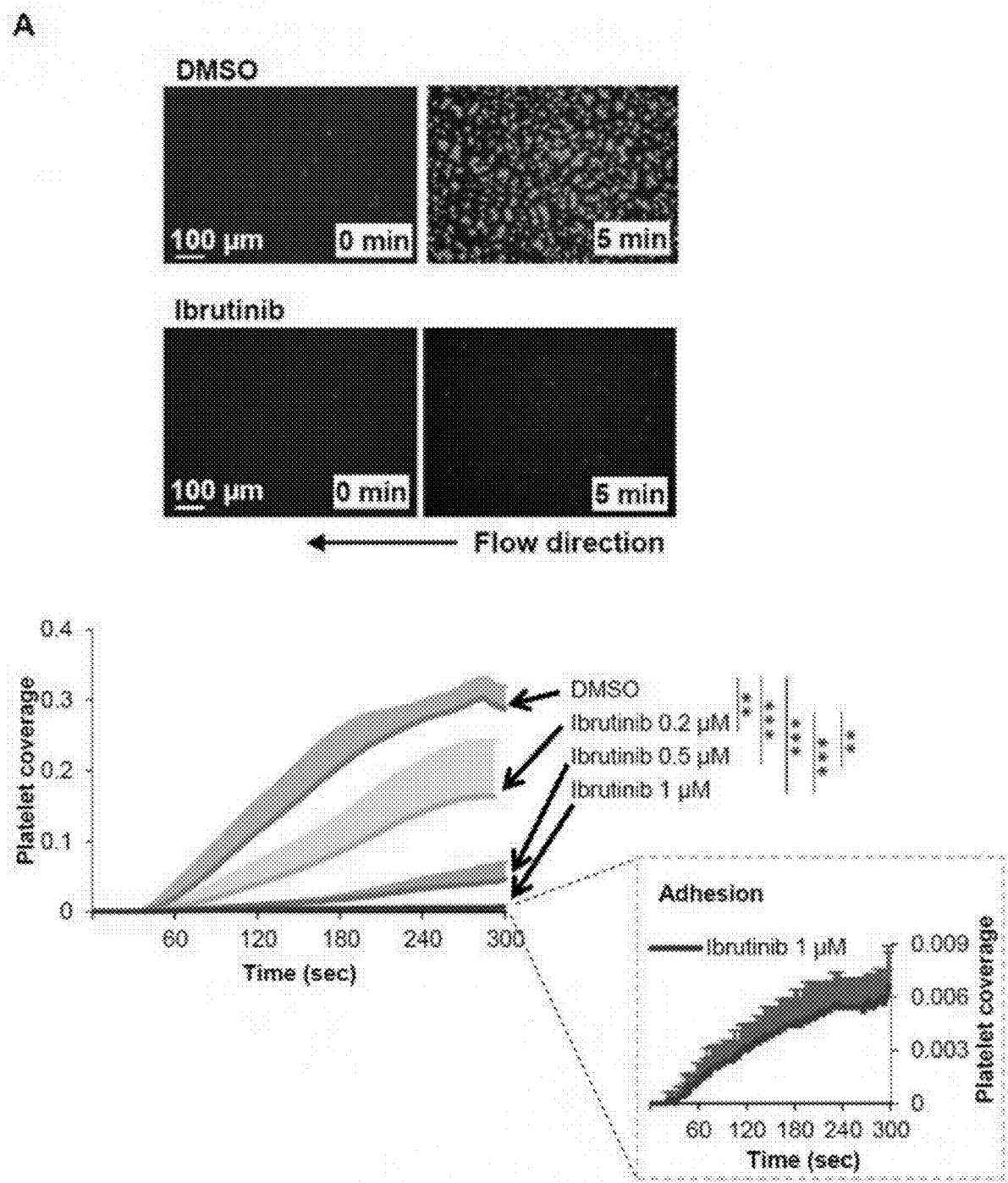
Figure 2:
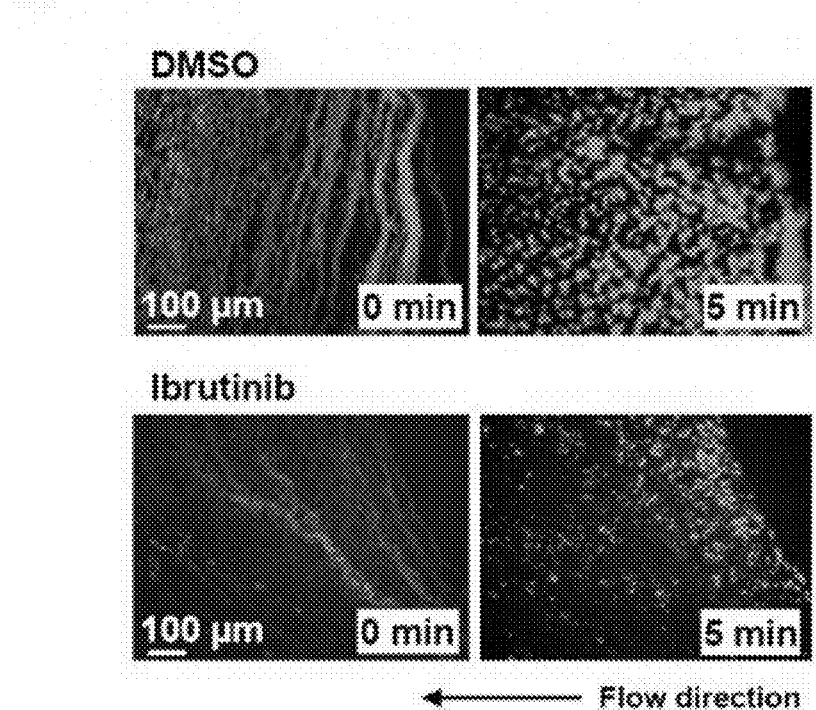
Figure 2:
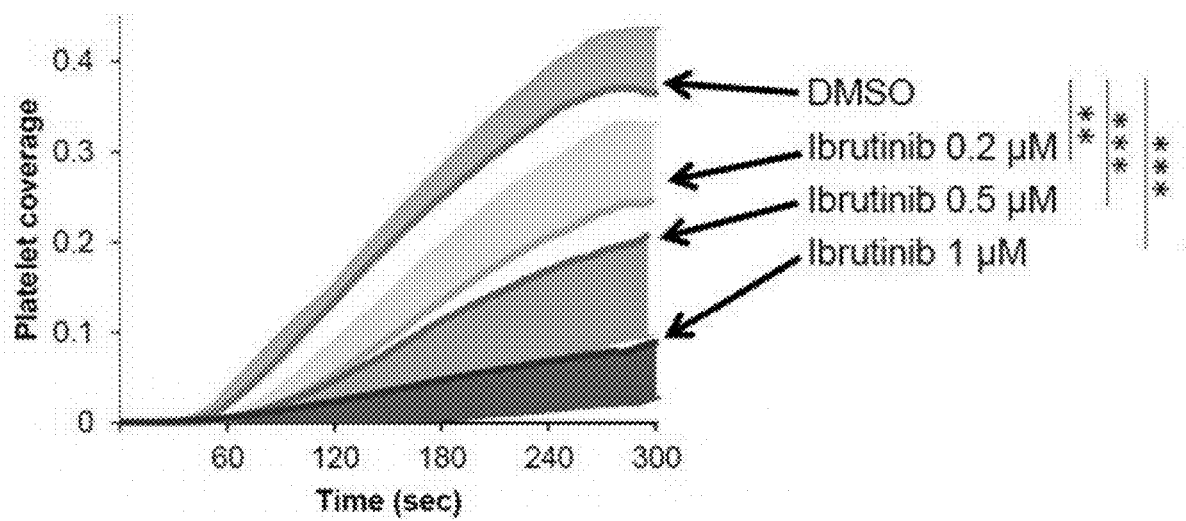
Figure 2:
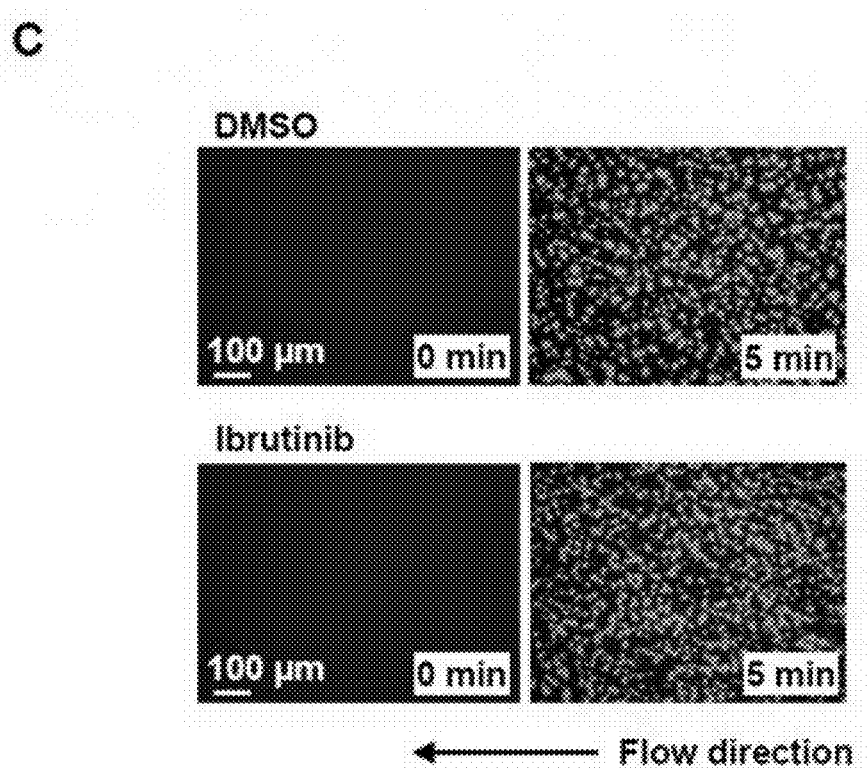
Figure 2:
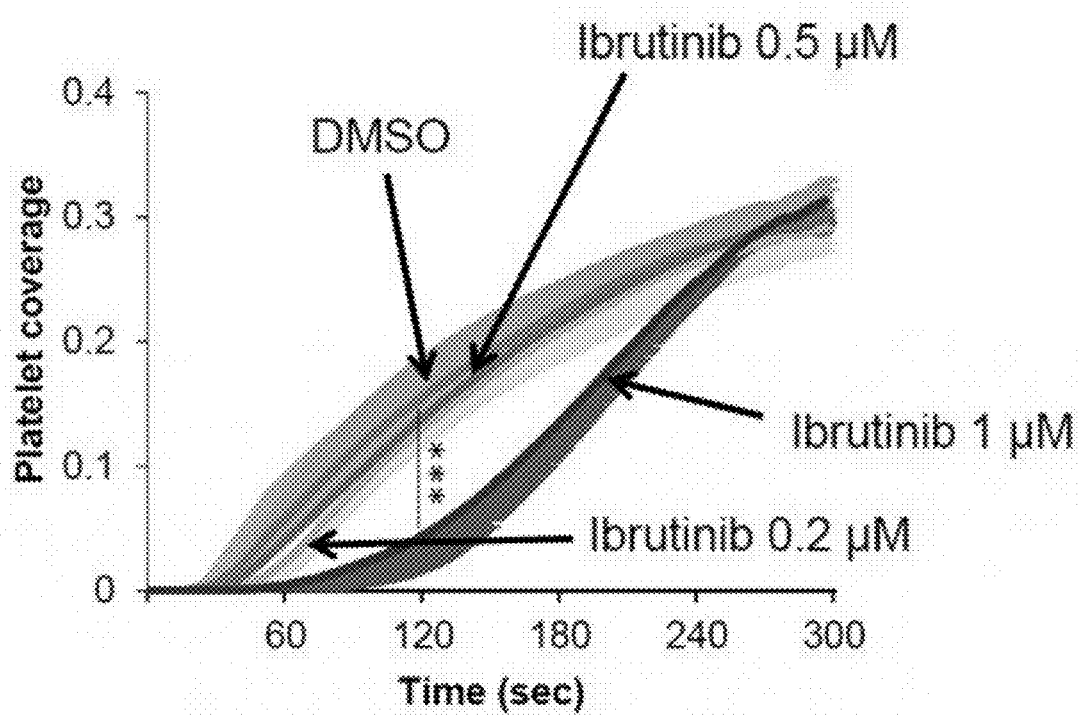
Figure 3:
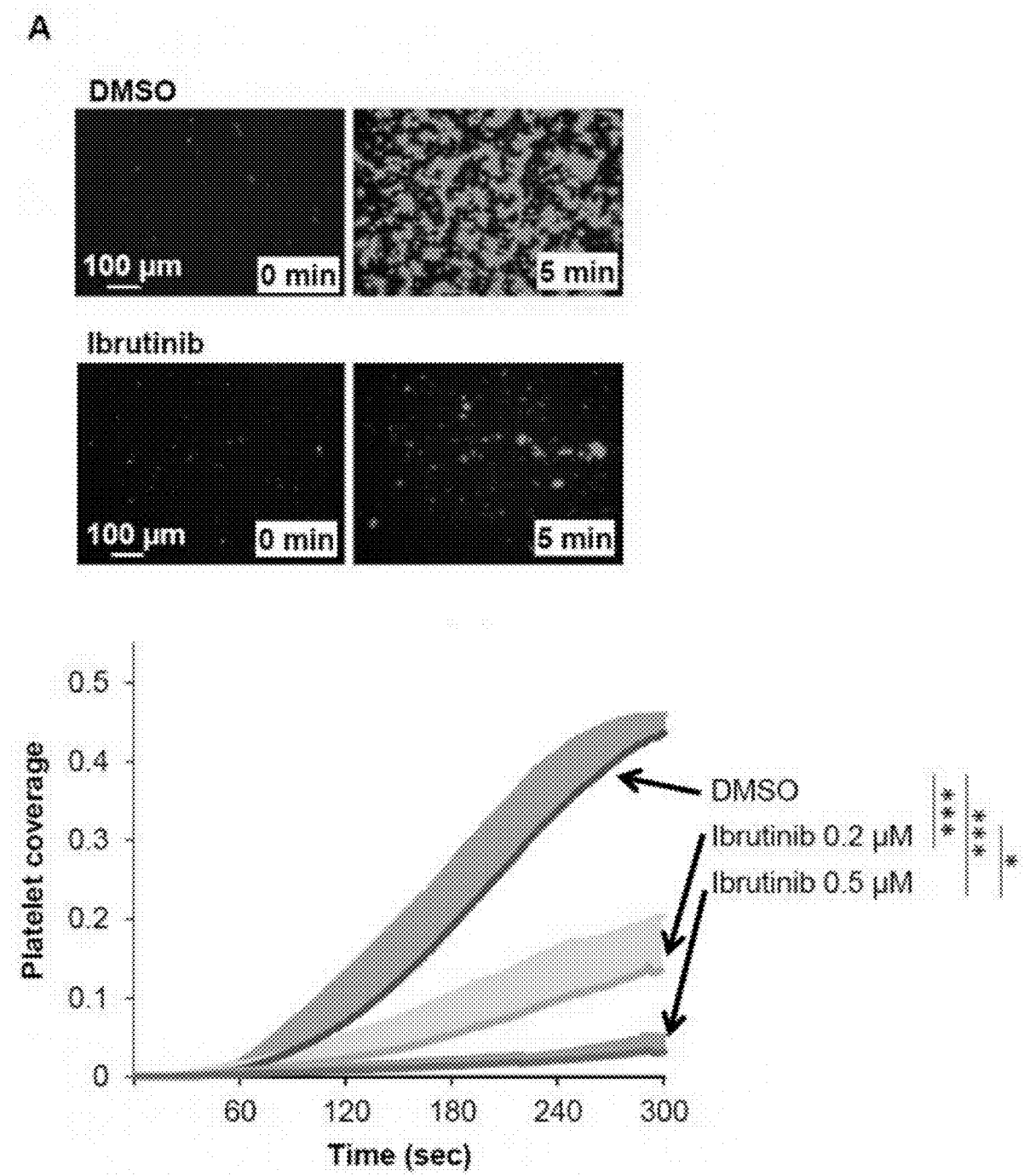
Figure 3:
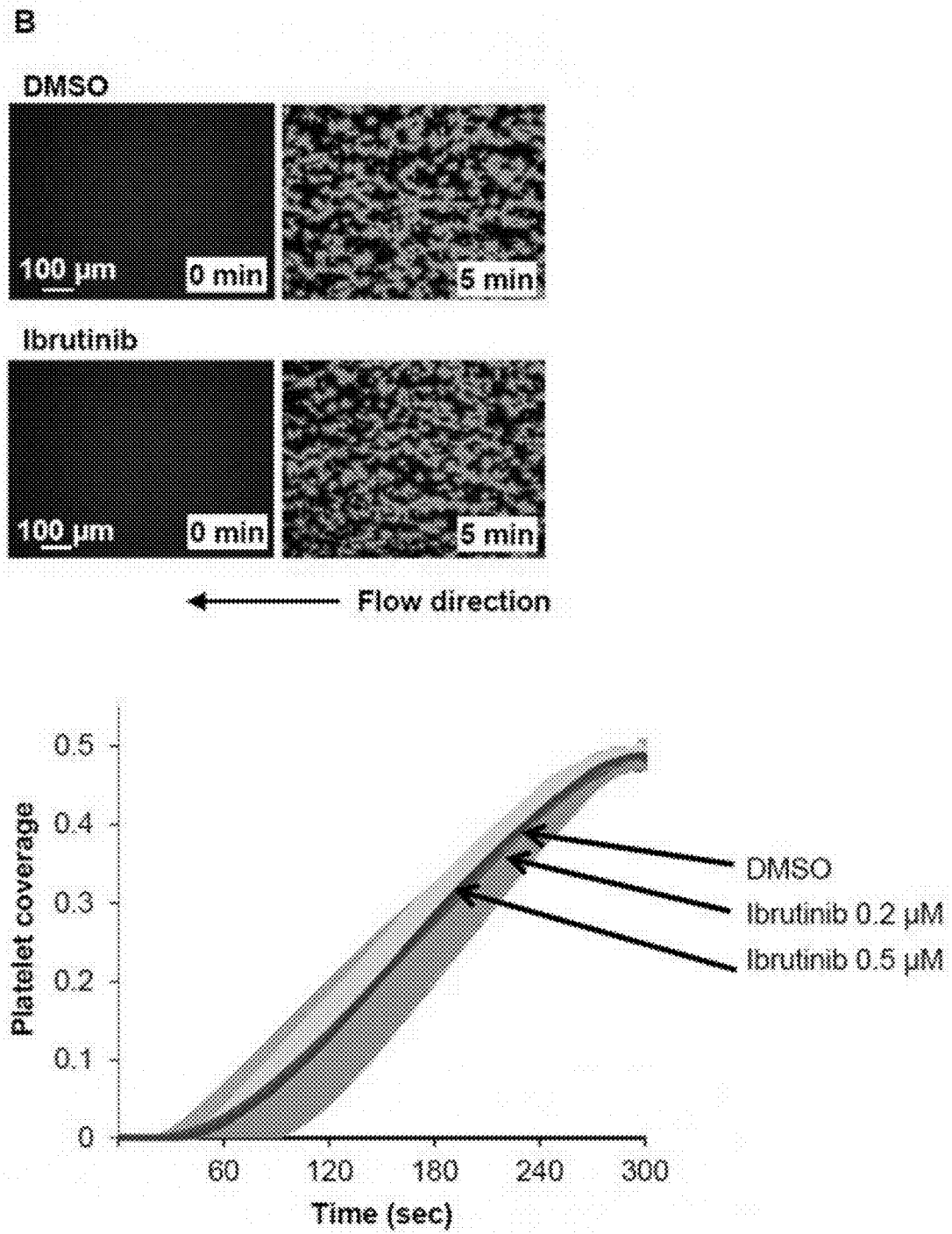

FIG. 2: Ibrutinib inhibits plaque- but not collagen-induced platelet aggregate formation under arterial flow at low shear rate (600/s). Blood samples were pre-incubated with DiOC6 for platelet labelling, and with solvent (0.1% DMSO) or ibrutinib for 15 min. Left, representative micrographs show the effect of solvent (0.1% DMSO) or ibrutinib (1 µM) on platelet deposition onto plaque homogenate (A), plaque tissue sections (B) and collagen (C) at 0 min and 5 min after start of blood flow. Right, the line diagrams show the effect of ibrutinib (0.2, 0.5 and 1 µM) on the kinetics of plaque- and collagen-induced platelet deposition. The inhibition of plaque-induced platelet deposition by ibrutinib (1 µM) is shown at blown-up scale in (A, bottom right). Values are mean±SD (n=5). Significances are indicated 5 min. after start of blood flow.

FIG. 3: Ibrutinib inhibits plaque- but not collagen-induced platelet aggregate formation under arterial flow at high shear rate (1500/s). Blood samples were preincubated with DiOC6 for platelet labelling, and with solvent (0.1% DMSO) or ibrutinib. Left, representative micrographs show the effect of solvent (0.1% DMSO) or ibrutinib (0.5 µM) on platelet deposition onto plaque homogenate (A) and collagen (B) at 0 min and 5 min after start of blood flow. Right, the line diagrams show the effect of ibrutinib (0.2, and 0.5 µM) on the kinetics of plaque- and collagen-induced platelet deposition. Values are mean±SD (n=5). Significances are indicated 5 min. after start of blood flow.

Figure 4:
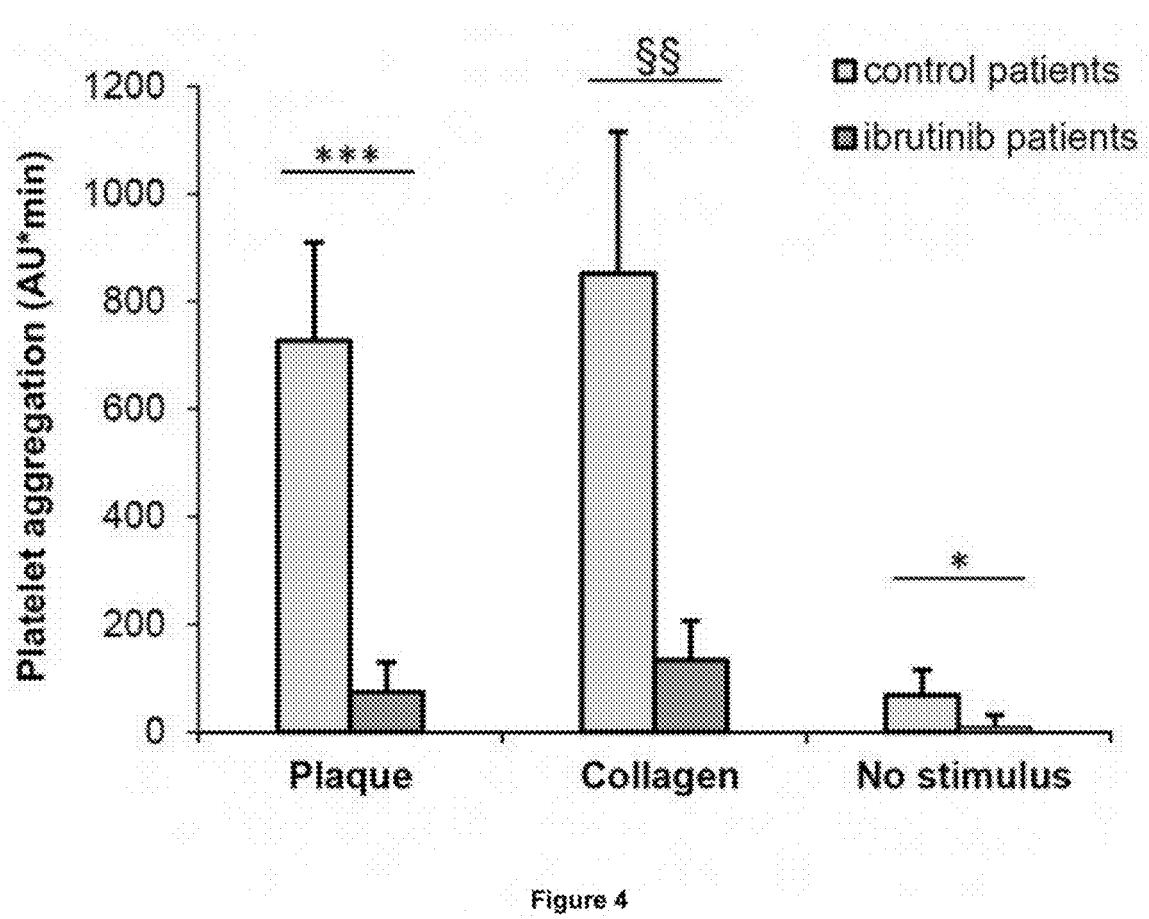

FIG. 4: Oral ibrutinib treatment inhibits plaque- and collagen-induced static platelet aggregation. Blood samples from patients treated with ibrutinib and from control patients were pre-incubated for 3 min at 37° C. before stimulation with plaque homogenate (833 µg/ml) or collagen (0.15-0.3 µg/ml) or without stimulation. Values are mean±SD (n=5).

Figure 5:
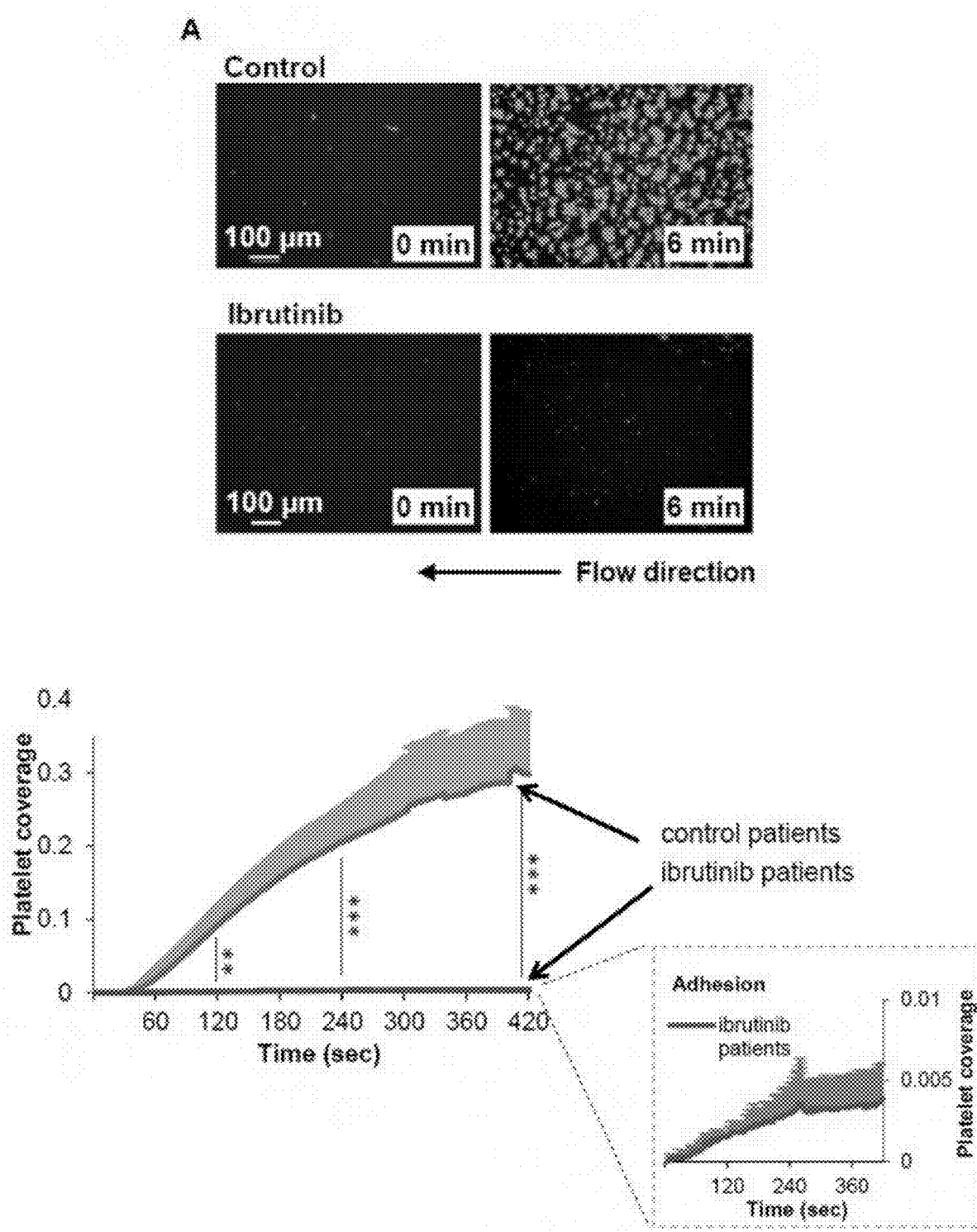
Figure 5:
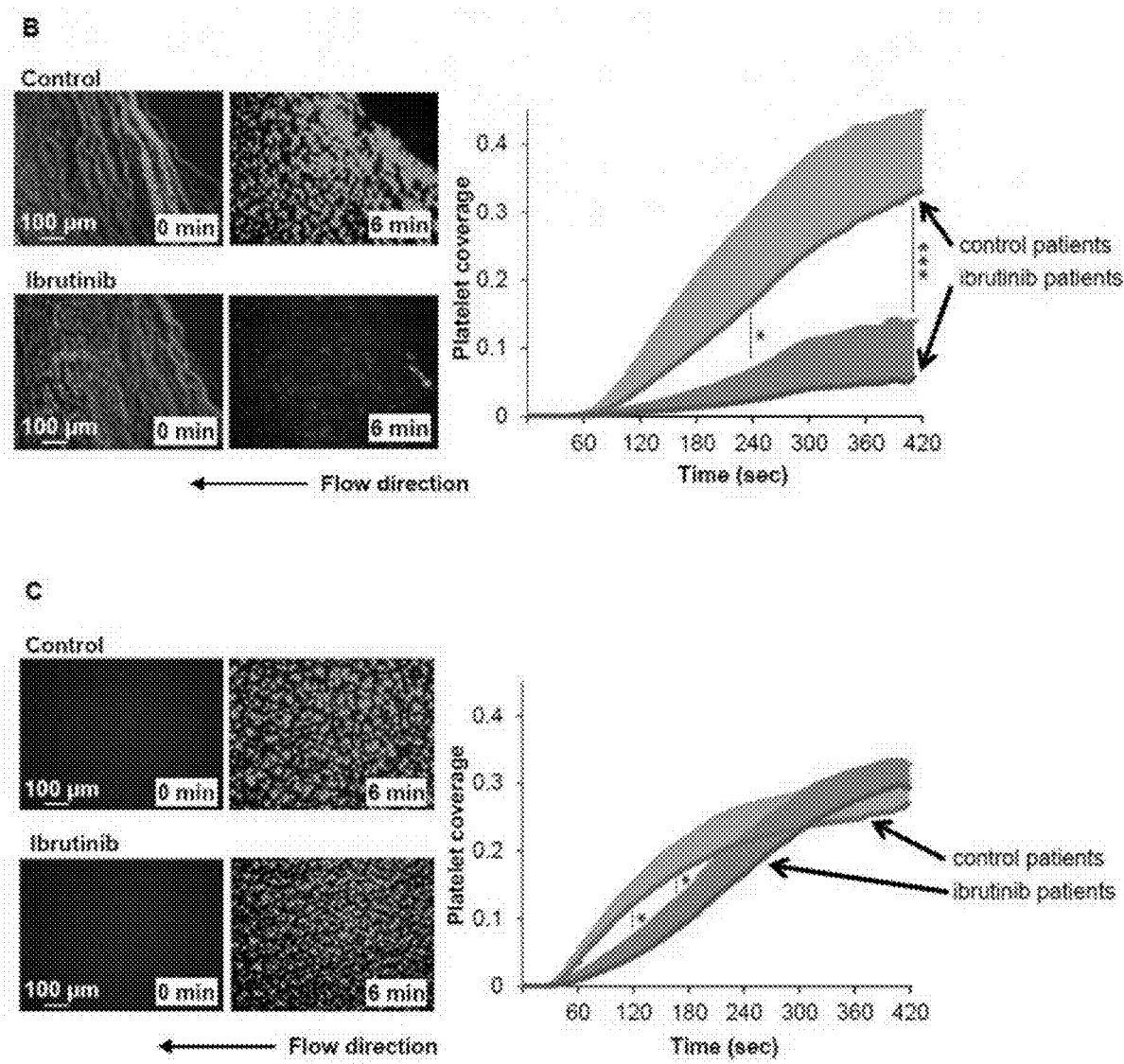

FIG. 5: Oral ibrutinib treatment inhibits platelet thrombus formation onto atherosclerotic plaque but not collagen under arterial flow. Left, representative micrographs show platelet coverage of plaque homogenate (A), plaque tissue sections (B) and collagen (C) at 0 min and 6 min after start of flow (shear rate 600/s) with blood from ibrutinib-treated patients and control patients. Right, the line diagrams show the effect of ibrutinib treatment of patients on the kinetics of plaque- and collagen-induced platelet deposition. Inhibition of plaque-induced platelet deposition by ibrutinib is shown at blown-up scale in (A, bottom right). Blood samples were pre-incubated with DiOC6 for platelet labelling for 10 min. Values are mean±SD (n=5).

Figure 6:
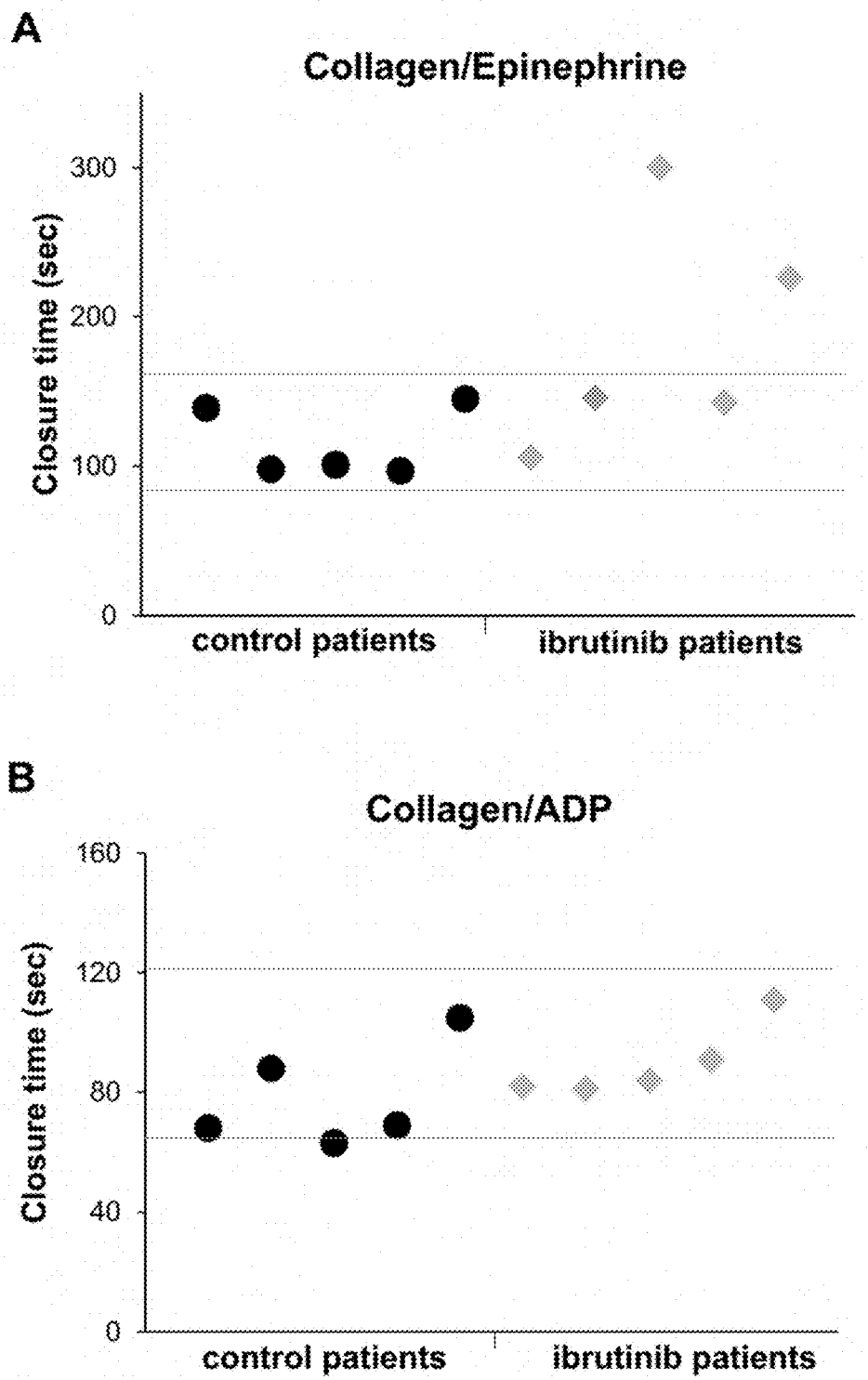
Figure 6:
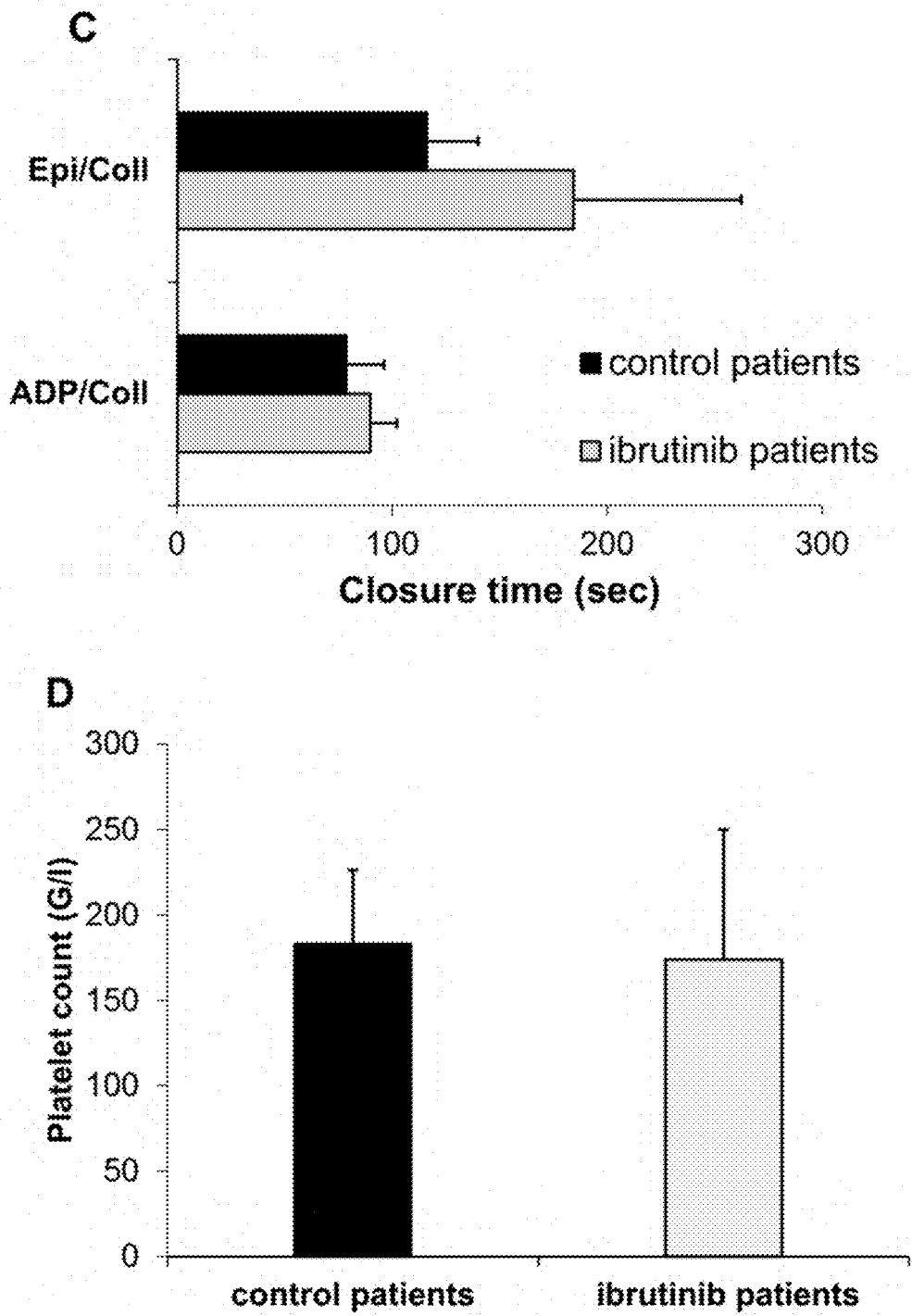

FIG. 6. Effect of oral ibrutinib treatment on bleeding time in vitro (PFA-100). Blood samples from 5 patients with ibrutinib treatment and 5 control patients were transferred to (A) collagen/epinephrine or (B) collagen/ADP cartridges, and the in vitro closure time was measured with the platelet function analyzer PFA 100®. (A, B) The result for each patient is shown. The two horizontal lines indicate the normal range (Coll/EPI 84-160 sec; Coll/ADP 68-121 sec). (C) Mean closure times of control and ibrutinib patients determined with the Collagen/Epi and Collagen/ADP cartridges. (D) Mean platelet counts (G/l) of control and ibrutinib patients. Values are mean±SD (n=5).

FIG. 7: The anti-α2β1 antibody 6F1, but not ibrutinib inhibits platelet adhesion onto immobilized soluble collagen under arterial flow. Blood was pre-incubated for 15 minutes at 37° C. before start of flow (shear 600/s) with DiOC6, abciximab (20 µg/ml), and either DMSO (0.1%; control), ibrutinib (1 µM) or 6F1 (20 µg/ml). Values are mean+SD (n=4).

FIG. 8: The anti-GPIbα antibody 6B4 inhibits plaque- and collagen-induced platelet aggregate formation under arterial flow at high shear rate (1500/s). Blood samples were pre-incubated with DiOC6, in the absence or presence of 6B4 (5 µg/ml) before perfusion. Effects of 6B4 on the kinetics of plaque- and collagen-induced platelet deposition. Values are mean+SD (n=4-5).

FIG. 9: Acalabrutinib (ACP-196) inhibits static platelet aggregation stimulated by plaque and collagen but not TRAP, ADP and arachidonic acid (AA). Blood samples were pre-incubated for 15 minutes with solvent (DMSO, 0.1%) or ACP-196 before stimulation with plaque (833 µg/ml), collagen (0.1-0.3 µg/ml), TRAP (5 µM), ADP (5 µM), AA or without stimulation. (A) Dose-response curve of ACP-196 on inhibition of plaque-induced platelet aggregation. (B) Effect of ACP-196 (2 µM) on plaque-, collagen-, TRAP-, ADP- and AA-induced platelet aggregation and spontaneous platelet aggregation. Values are mean±SD (n=4)

FIG. 10: ONO/GS-4059 inhibits static platelet aggregation stimulated by plaque and collagen but not TRAP, ADP and arachidonic acid (AA). Blood samples were pre-incubated for 15 minutes with solvent (DMSO, 0.1%) or ONO/GS-4059 before stimulation with plaque (833 µg/ml), collagen (0.1-0.3 µg/ml), TRAP (5 µM), ADP (5 µM), AA (0.6 mM) or without stimulation. (A) Dose-response curve of ONO/GS-4059 on inhibition of plaque-induced platelet aggregation. (B) Effect of ONO/GS-4059 (2 µM) on plaque-, collagen-, TRAP-, ADP- and AA-induced platelet aggregation and spontaneous platelet aggregation. Values are mean±SD (n=5)

FIG. 11: Acalabrutinib (ACP-196) inhibits plaque- but not collagen-induced platelet thrombus formation under arterial flow. Blood samples were pre-incubated with DiOC6 for platelet labelling, and with solvent (0.1% DMSO) or increasing concentrations of ACP-196 (all in DMSO, final concentration 0.1%) for 15 min before start of blood flow at a shear rate of 600/s. The line diagrams show the effect of ACP-196 (0.5, 1 and 2 µM) on the kinetics of plaque- and collagen-induced platelet deposition. Values are mean+SD (n=3). Significances are indicated 5 min. after start of blood flow.

FIG. 12: ONO/GS-4059 inhibits plaque- but not collagen-induced platelet thrombus formation under arterial flow. Blood samples were pre-incubated with DiOC6 for platelet labelling, and with solvent (0.1% DMSO) or increasing concentrations of ONO/GS-4059 (all in DMSO, final concentration 0.1%) for 15 min before start of blood flow at a shear rate of 600/s. The line diagrams show the effect of ONO/GS-4059 (0.5, 1 and 2 µM) on the kinetics of plaque- and collagen-induced platelet deposition. Values are mean+SD (n=3). Significances are indicated 5 min. after start of blood flow.

FIG. 13: DMSO does not impair plaque- and collagen-induced platelet deposition under arterial flow. Blood was pre-incubated with NaCl or DMSO (0.1%) for 15 minutes at 37° C. before start of flow (shear 600/s). Values are mean±SD (n=5).

FIG. 14: Oral intake of an Imbruvica® loading dose (3×140 mg) inhibits 3 hours later static platelet aggregation stimulated by plaque and collagen but not TRAP, ADP and arachidonic acid (AA). Blood was taken from two blood donors A and B before (control) and 3 h after intake of Imbruvica® (ibrutinib) 3×140 mg, and stimulated with two different pools of plaque homogenate A and B (833 µg/ml), collagen (0.2 µg/ml), TRAP (5 µM), ADP (5 µM), or AA (0.6 mM). Aggregation in blood was measured by MEA. Values are mean+SD of triplicates.

FIG. 15: Oral intake of low doses of Imbruvica® for 1 week suppress static platelet aggregation stimulated by plaque and collagen, but not by ADP and arachidonic acid (AA). Blood was taken before (control) and 1 week after intake of Imbruvica® (ibrutinib) (donor A, 140 mg/d; donor B, 140 mg each second day), and stimulated with two different pools of plaque homogenate A and B (833 µg/ml), collagen (0.2 µg/ml), TRAP (5 µM), ADP (5 µM), or AA (0.6 mM). Values are mean+SD of triplicates.

FIG. 16: Rapid and continuous suppression of plaque-induced platelet aggregation by a loading and low maintenance dose of Imbruvica®. Blood was taken before (control), 3 h after intake of Imbruvica® (ibrutinib) 3×140 mg, and at different days after intake of Imbruvica® (140 mg/d). Samples were stimulated with plaque homogenate (833 µg/ml), ADP (5 µM), or not. Values are mean of duplicates.

Figure 17B:
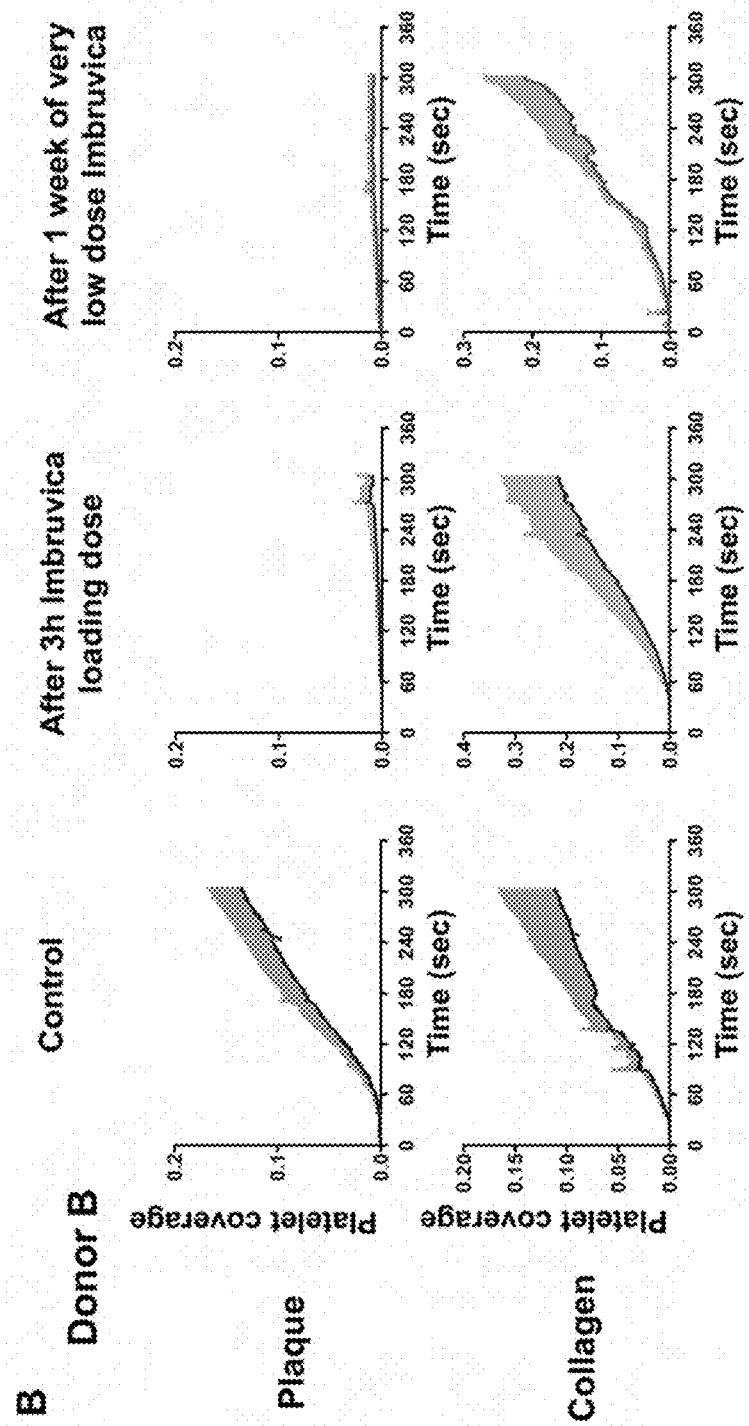

FIG. 17: Rapid and continuous suppression of plaque- but not collagen-induced platelet thrombus formation under arterial flow by a loading and low maintenance dose of Imbruvica® for 1 week. Blood was taken from donor A before (control), 3 h after intake of Imbruvica® (ibrutinib) 3×140 mg, and after 1 week of Imbruvica® (140 mg/d) (A). Blood was taken from donor B before (control), 3 h after intake of Imbruvica® (ibrutinib) 3×140 mg, and after 1 week of Imbruvica® (140 mg each other day (B). Samples were pre-incubated with DiOC6 for platelet labelling for 10 min before start of blood flow at a shear rate of 600/s. The line diagrams show the effect of Imbruvica® intake on the kinetics of plaque- and collagen-induced platelet deposition. Values are mean+SD of triplicates.

Figure 18:
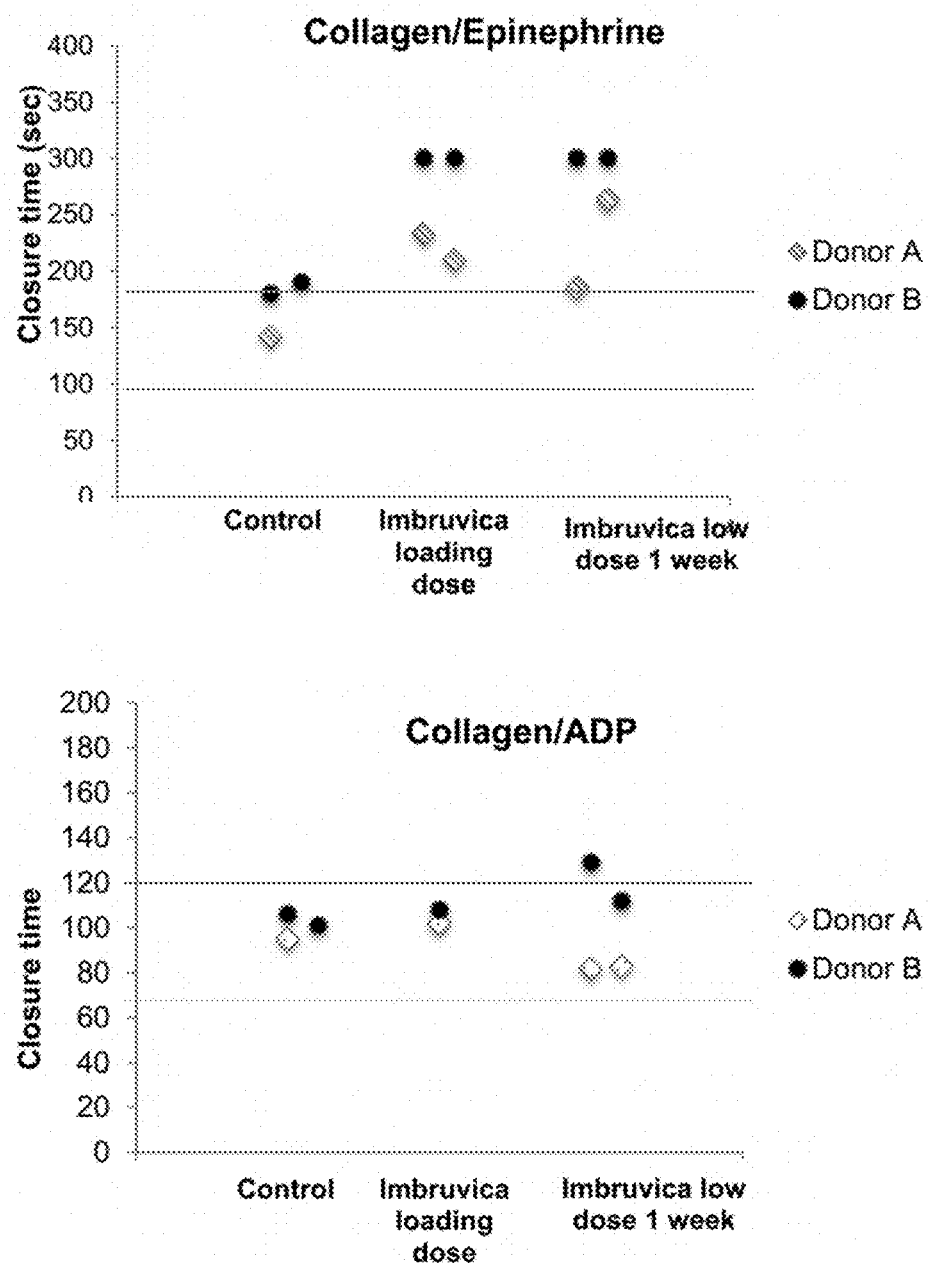

FIG. 18 Effect of a loading and low maintenance dose of Imbruvica® for 1 week on bleeding time in vitro (PFA-200). Blood samples from donor A and donor B were taken before (control), 3 h after Imbruvica® (ibrutinib) 3×140 mg, and after 1 week of Imbruvica® (140 mg/d: donor A; 140 mg each other day: donor B), and transferred to (A) collagen/epinephrine or (B) collagen/ADP cartridges. The in vitro closure time was measured with the platelet function analyzer PFA 1008. The two horizontal lines indicate the normal range (Coll/EPI 84-170 sec; Coll/ADP 68-120 sec). Values are single measurements.

The examples illustrate the invention.

EXAMPLE 1: MATERIALS AND METHODS

Reagents

Ibrutinib, acalabrutinib (ACP-196) and ONO/GS-4059 were obtained from Selleckchem (Houston, USA). Dimethyl sulfoxide (DMSO) and albumin from human serum (fatty acid free) came from Sigma-Aldrich (Taufkirchen, Germany). Collagen (Horm) and diluting solvent were purchased from Takeda (Linz, Austria). Thrombin receptor activating peptide (TRAP) was obtained from Bachem AG (Bubendorf, Switzerland). 3'-phosphate 5'-phosphate (ADP) came from Biopool (Wicklow, Ireland). DiOC6 was obtained from Life Technologies (Eugene, Oreg., USA). PBS (Dulbecco's Phosphate Buffered Saline) was from Gibco (Grand Island, N.Y., USA). Recombinant lepirudin (Refludan®) came from Celgene (Windsor, UK). Tissue-Tek® as embedding medium for cryotomy came from Sakura (Alphen aan den Rijn, the Netherlands).

Stock Solutions

Ibrutinib. acalabrutinib (ACP-196) and ONO/GS-4059 were dissolved in dimethyl sulphoxide (DMSO) at a concentration of 20 mM. Aliquots (30 µl) were stored at −80° C. Before each in vitro experiment, dilutions were made in DMSO (0.1, 0.2, 0.5, 1 and 2 mM) to obtain final concentrations in blood of 0.1 µM, 0.2 µM, 0.5 µM, 1 µM and 2 µM, respectively. The final concentration of DMSO in blood was 0.1%. Collagen (1000 µg/ml) was diluted in diluting solvent in a 1:10 ratio (100 µg/ml) for aggregometry experiments or in a 1:50 ratio (20 µg/ml) for flow experiments. TRAP was dissolved in 0.9% NaCl at a concentration of 500 µM. ADP was dissolved in aqua destillata at a concentration of 500 µM. DiOC6 for platelet labeling was dissolved in DMSO at a concentration of 5 mM. Aliquots (10 µl) were stored at −20° C. Before each flow experiment, stock solution was dissolved in human serum albumin (HSA, 0.5% in PBS) at a concentration of 100 µM to obtain final concentration in blood sample of 1 µM.

Human Carotid Atherosclerotic Plaques

Atherosclerotic tissue specimens were donated from patients who underwent endarterectomy for high-grade carotid artery stenosis as described previously (Brandi R. et al., *Circulation.* 1997; 96:3360-3368; Reininger A J. et al., *J Am Coll Cardiol.* 2010; 55:1147-11585; Penz S. et al. *Faseb J.* 2005; 19:898-909). Patient consent was obtained as approved by the Ethics Committee of the Faculty of Medicine of the University of Munich. The specimens containing lipid-rich plaques were collected. The atheromatous plaques were carefully dissected under sterile conditions from other regions of the atherosclerotic tissue specimens (Brandl R. et al., *Circulation.* 1997; 96:3360-3368; Reininger A J. et al., *J Am Coll Cardiol.* 2010; 55:1147-11585; Penz S. et al. *Faseb J.* 2005; 19:898-909). The plaques were processed to obtain either homogenates or serial tissue sections.

For plaque homogenates, the plaque specimens were weighed, homogenized in buffer (150 mM NaCl, 1 mM EDTA, pH 7.4) adjusted to a concentration of 100 mg wet weight/ml and stored at −80° C. Plaque homogenates from 5 patients were pooled (Dwivedi S. et al., *J Transl Med.* 2010; 8:128). Pooled plaque homogenates were diluted with PBS for the static tests in the Multiplate® analyzer in a 1:1 ratio and for the flow experiments in a 1:20 ratio.

For sequential plaque tissue sections, atherosclerotic tissue specimens from 4 different patients were embedded in Tissue-Tek®, transversely cut into 3 microns thin sections at −20° C. by cryostat (Leica C M 3050S, Wetzlar, Germany) and coated onto glass cover-slips. The tissue sections were stored at −80° C.

Blood Collection

For experiments of ibrutinib addition in vitro, blood was obtained from healthy adults who had not taken any medication affecting platelet function for at least 2 weeks preceding the experiment.

For ex vivo experiments, CLL patients (n=5) on continuous ibrutinib treatment (Imbruvica, 3×140 mg capsules daily, Janssen Pharmaceutica NV, B-2340 Beerse, Belgium) and control patients (n=5) with platelet counts higher than 150 G/l were selected in order to allow analysis of platelet function in blood unimpaired by its platelet concentration. Four of the control patients had CLL, one had MCL, and were not in need of treatment. For each experimental day, a pair of one ibrutinib and control patient with similar platelet counts was chosen, and their platelet functions were tested in parallel. Patients' informed consent was obtained in accordance with the Helsinki protocol.

Blood was taken by venipuncture using a 21-gauge needle and plastic syringe containing 1/10 volume recombinant hirudin dissolved in 0.9% NaCl (final concentration in blood ~200 U/ml; 13 µg/ml). The first 3 ml of blood drawn into an empty syringe were discarded. Experiments were performed between 30 min and 4 h after venipuncture.

Platelet Aggregation in Blood

Platelet aggregation in blood was measured by multiple electrode aggregometry (MEA) using the Multiplate® device from Dynabyte (Munich, Germany) (Toth O. et al. *Thromb Haemost.* 2006; 96:781-8). Ibrutinib, acalabrutinib (ACP-196), or ONO/GS-4059 (0.1, 0.2, 0.5, 1 or 2 µM) or DMSO (0.1%, control) were first added to 0.3 ml of physiological saline in the MEA cuvettes before addition of 0.3 ml of blood. The samples were pre-incubated in the absence of stirring for 15 minutes in the test cuvettes. In the ex vivo experiments with the patients' blood, the samples were pre-incubated in the absence of stirring for 3 minutes at 37° C. (Bampalis V G. et al. *J Thromb Haemost.* 2012; 10:1710-4). Subsequently plaque homogenate (833 µg/ml) or collagen (0.2-0.4 µg/ml; as tested in individual blood donors to induce the same aggregation values as plaque homogenate), TRAP (5 µM) or ADP (5 µM) was added, stirring was started, and the impedance change was recorded continuously for 10 minutes in duplicate samples. Cumulative aggregation values over the 10 min time period are expressed as AU*min (AU, aggregation unit).

Analysis of Platelet Aggregation and Thrombus Formation in Flowing Whole Blood

For experiments in flowing blood, glass cover slips (Menzel, 24×60 mm, #1.5) coated with collagen (20 µg/ml), plaque homogenates or plaque tissue sections were assembled into parallel plate flow chambers using sticky slides (0.1 Luer sticky slides, Ibidi®, Martinsried, Germany) which had been blocked before with human serum albumin (HSA; 4% in PBS). The flow chamber was then mounted on the stage of a fluorescence microscope (TE2000-E, Nikon, Tokyo, Japan) equipped with an incubation chamber (37° C.). The flow chambers were perfused with PBS and subsequently blocked with PBS containing 4% HSA for 2 min to prevent non-specific binding of platelets to the glass cover slips.

Ibrutinib, acalabrutinib (ACP-196), or ONO/GS-4059 (0.1, 0.2, 0.5, 1 or 2 µM) or DMSO (final concentration in blood 0.1%; control) was first added to 100 µl of NaCl (0.9%) placed in Falcon tubes, and blood samples (2 ml) were subsequently added. This procedure avoided haemolysis and guaranteed that ibrutinib was entirely in the blood samples. DiOC6 (1 µM) was added to blood for fluorescence labeling of platelets, and the samples were incubated for 15 min at 37° C.[7] Control runs were performed with DMSO or NaCl alone. In the ex vivo experiments, 3 ml of blood from patients with or without ibrutinib treatment were pre-incubated with DiOC6 (1 µM) for 10 min at 37° C.

Blood was perfused through the flow chamber at two shear rates (600/s; 1500/s) with a withdrawal syringe pump (Harvard Apparatus, Holliston, Mass., USA) (Jamasbi J. et al. *J Am Coll Cardiol.* 2015; 65:2404-15). Fluorescence microscopy (excitation: 485/25 nm, emission: 528/38 nm) was performed for real time measurement of platelet adhesion and aggregate formation using a 10× air objective (NA 0.4) and a CoolSNAP HQ2 CCD camera (Photometrics, Tucson, USA). Fluorescence images were continuously recorded (1 frame/sec) for 5 to 7 min. They were analyzed by quantifying the binary fluorescent area fraction (1.0=total area) after subtraction of the plaque autofluorescence at time 0 min using the NIS-element 3.2 (Nikon, Tokyo, Japan) software package (Jamasbi J. et al. *J Am Coll Cardiol.* 2015; 65:2404-15). The area visualized in this setting was 669 µm×896 µm (Jamasbi J. et al. *J Am Coll Cardiol.* 2015; 65:2404-15). Values are the mean±SD (measured each sec) of 5 experiments for each inhibitor with blood from different donors (Jamasbi J. et al. *J Am Coll Cardiol.* 2015; 65:2404-15).

Analysis of In Vitro Closure Time (CT) in Whole Blood

The PFA 100° and PFA 200® devices (Siemens Healthcare, Erlangen, Germany) are a further development of the Thrombostat system which simulates primary haemostasis and is used to measure bleeding time in vitro (Kratzer M A. et al. *Semin Thromb Hemost.* 1995; 21 Suppl 2:25-31; Kundu S K, et al. *Semin Thromb Hemost.* 1995; 21 Suppl 2:106-12). The instrument aspirates citrate-anticoagulated blood (0.8 ml) under constant vacuum from a reservoir through a capillary and a small hole in a membrane filter which is coated with collagen and ADP (collagen/ADP test cartridge), or collagen and epinephrine (collagen/EPI test cartridge). The time required to obtain full occlusion of the aperture is reported as "in vitro closure time". Closure times were measured in two healthy donors, five patients with or without ibrutinib treatment. The five ibrutinib patients were the same as tested above in the static and flow experiments.

Statistics

Means of two parallel experimental conditions were compared by paired Student's t-test (*: $p<0.05$; : $p<0.01$, *: $p<0.001$). More than two concurrent experimental conditions were tested by ANOVA for repeated measures followed by pair comparisons by Bonferroni's test (§: $p<0.05$; §§: $p<0.01$, §§§: $p<0.001$).

EXAMPLE 2: IBRUTINIB INHIBITS PLAQUE- AND COLLAGEN-INDUCED PLATELET AGGREGATION IN BLOOD UNDER STATIC CONDITIONS

Pre-incubation of blood with ibrutinib (1 µM) almost completely inhibited platelet aggregation upon stimulation with plaque and collagen as measured by impedance aggregometry (FIG. 1A). Inhibition of platelet aggregation stimulated by plaque and collagen by ibrutinib showed similar dose-response curves. The IC50 values of ibrutinib for inhibition of plaque- and collagen-stimulated platelet aggregation were 0.18±0.05 µM, and 0.12±0.04 µM, respectively, and maximal suppression was reached at 0.5 µM (FIG. 1B, C). In contrast, ibrutinib reduced platelet aggregation stimulated by TRAP activating the PAR-1 receptor and ADP only modestly (by −31%, and −13%, respectively; FIG. 1A, D). Even spontaneous minimal platelet aggregation in the absence of stimuli was abolished by ibrutinib (FIG. 1A, bottom, D).

EXAMPLE 3: IBRUTINIB INHIBITS PLATELET THROMBUS FORMATION UNDER ARTERIAL FLOW CONDITIONS STIMULATED BY PLAQUE HOMOGENATE AND PLAQUE TISSUE, BUT NOT BY COLLAGEN

To simulate platelet activation by plaque rupture, human blood was perfused in a parallel plate flow chamber over coverslips coated with human plaque homogenate or plaque tissue sections at physiological wall shear rates of healthy carotid and coronary arteries (600/s) and at rates over mildly stenotic coronary lesions (1500/s).

At 600/s, ibrutinib (1 µM) completely abolished platelet aggregation onto plaque homogenate (−98±1%), whilst preserving platelet adhesion (FIG. 2A). Ibrutinib (1 µM) also strongly inhibited platelet thrombus formation onto plaque tissue (by −76±16%; FIG. 2B), but only delayed and did not compromise final platelet aggregate formation (+8±2%) onto collagen fibers (FIG. 2C). Lower concentrations of ibrutinib (0.2 and 0.5 µM) still delayed and reduced platelet aggregation onto plaque homogenate (−43±27 and −84±8%, respectively) and plaque tissue (−33±23 and −44±30%, respectively), but did not impair collagen-induced platelet aggregation (+1±6 and +3±9%, respectively). DMSO solvent did not affect platelet aggregation (data not shown).

Even at high shear rate, ibrutinib (0.2 µM and 0.5 µM) did not reduce platelet aggregation onto collagen, but still inhibited platelet thrombus formation onto plaque homogenate (by −69±16% and −93±5%, respectively), (FIG. 3).

EXAMPLE 4: PLAQUE- AND COLLAGEN-INDUCED PLATELET AGGREGATION UNDER STATIC AND ARTERIAL FLOW CONDITIONS IN PATIENTS ON IBRUTINIB THERAPY

Next, the effect of ongoing ibrutinib therapy (420 mg/d) in five CLL patients was analyzed. Five matched patients not taking ibrutinib served as control. Blood platelet counts were similar in patients on ibrutinib (174±19 G/l) and in controls (186±37 G/l). In blood from patients on ibrutinib, platelet aggregation was inhibited when stimulated in vitro under static conditions by plaque (−89±7%) or collagen (−84±8%), and even unstimulated spontaneous platelet aggregation was blocked (FIG. 4). Of note, ibrutinib treatment abolished platelet thrombus formation onto plaque homogenate under arterial flow conditions, whilst preserving platelet adhesion (FIG. 5A). Also platelet thrombus formation onto plaque tissue was largely prevented (by −83±24%; FIG. 5B). In contrast, ibrutinib only minimally slowed down initial platelet aggregation from flowing blood onto collagen fibers but reached the same maximal response as in controls (FIG. 5C).

EXAMPLE 5: EFFECT OF IBRUTINIB EX VIVO ON IN VITRO CLOSURE TIME (CT)

To test whether ibrutinib intake might increase bleeding time, measurements were performed with the platelet function analyzer PFA-100 in the same five patients taking ibrutinib as tested above. This device simulates primary haemostasis in vitro. It is, however, still a matter of debate, whether abnormal values found with the PFA-100 or PFA-200 devices reflect potential bleeding risk in vivo (Kundu S K. et al., *Semin Thromb Hemost.* 1995; 21 Suppl 2:106-112; Paniccia R. et al., *Vascular health and risk management.* 2015; 11:133-148). The mean closure time in the patients on ibrutinib therapy was not significantly increased, but two out of five patients showed a prolonged closure time with the collagen/epinephrine test cartridge (FIG. 6A, C). With the collagen/ADP Cartridge, closure time was in the normal range in both patient groups (FIG. 6B, C). Blood platelet counts were similar in both patient groups (FIG. 6D)

EXAMPLE 6: IBRUTINIB INHIBITS PLATELET AGGREGATION ONTO PLAQUE UNDER ARTERIAL FLOW THROUGH MECHANISMS INDEPENDENT OF PLATELET INTEGRIN α2β1 AND GPIb BINDING TO VWF

Under arterial flow, the integrin $\alpha_2\beta_1$-blocking antibody 6F1 but not ibrutinib blocked platelet adhesion onto soluble type I collagen (FIG. 7). This confirms that the integrin $\alpha_2\beta_1$ is critical for platelet adhesion to soluble collagen (Jung and Moroi *J Biol Chem* (1998)273(24):14827-37), and demonstrates that ibrutinib does not interfere with the integrin $\alpha_2\beta_1$-mediated platelet adhesion to native collagen in physiologic hemostasis.

To further clarify whether the plaque-specific inhibition of platelet aggregation by ibrutinib at high shear flow is only due to inhibition of GPVI-signaling or also of GPIb signaling, blood was preincubated with the monoclonal antibody 6B4 which inhibits the interaction of GPIbα with VWF (Penz S M et al *Thromb Haemost* (2007); 97(3):435-43. When perfused over plaque homogenate and collagen at high shear, both plaque homogenate- and collagen-induced platelet thrombus formation were equally well inhibited (>95%) (FIG. 8). This indicates that VWF activation of GPIb is required for platelet adhesion and aggregation to both plaque and collagen surfaces under high shear rate, but also implies that Btk-signaling downstream GPIb is not functionally relevant here.

EXAMPLE 7: THE NEW $2^{ND}$ GENERATION BTK INHIBITORS ACALABRUTINIB (ACP-196) AND ONO/GS-4059 INHIBIT PLAQUE- AND COLLAGEN-INDUCED PLATELET AGGREGATION IN BLOOD UNDER STATIC CONDITIONS

Pre-incubation of blood with acalabrutinib (ACP-196) and ONO/GS-4059 dose-dependently inhibited plaque-induced platelet aggregation in blood as measured by impedance aggregometry (FIG. 9A; FIG. 10A). The IC50 values of ACP-196 and ONO/GS-4059 were 0.4 µM, and 1 µM, respectively, and maximal suppression (80% and 82%, respectively) was reached at 1 and 2 µM, respectively. Collagen-induced platelet aggregation was equally well inhibited (FIG. 9B, FIG. 10B). In contrast, ACP-196 (2 µM) and ONO/GS-4059 (2 µM) reduced platelet aggregation stimulated by TRAP, ADP or AA only marginally (FIG. 9B, FIG. 10B). The spontaneous minimal platelet aggregation in the absence of stimuli was abolished by ibrutinib (FIG. 1A, bottom, D).

EXAMPLE 8: ACALABRUTINIB (ACP-196) AND ONO/GS-4059 INHIBIT PLATELET THROMBUS FORMATION UNDER ARTERIAL FLOW CONDITIONS STIMULATED BY PLAQUE HOMOGENATE, BUT NOT BY COLLAGEN

ACP-196 dose-dependently inhibited platelet aggregation onto plaque homogenate at arterial flow with a shear rate of 600/s, and 2 µM inhibited platelet aggregation by 96% (FIG. 11). Also ONO/GS-4059 showed a dose-dependent inhibition, and at 2 µM strongly inhibited platelet thrombus formation onto plaque homogenate by −76%; FIG. 12). Both Btk inhibitors only delayed at the highest concentrations tested, but did not compromise final platelet aggregate formation onto collagen fibers (FIGS. 11,12). DMSO solvent did not affect platelet aggregation (FIG. 13).

EXAMPLE 9: ORAL INTAKE OF LOW DOSES OF IBRUTINIB INHIBITS PLAQUE-INDUCED PLATELET AGGREGATION UNDER STATIC CONDITIONS AND ARTERIAL FLOW

To test ibrutinib as possible antiplatelet therapy, two healthy physicians (male, 61 and 66 years old) took a loading dose of Imbruvica (3 capsules×140 mg=420 mg), followed by a low dose of 140 mg/d for 1 week (donor A) or a very low dose of 140 mg each other day for 1 week (donor B). This regimen was without any adverse side effects in the two donors.

The loading dose 3×140 mg Imbruvica almost completely inhibited platelet aggregation induced by two plaque homogenate pools by 94% and 93%, and by collagen by 91% in donor A, and reduced platelet aggregation by 68% and 77% after plaque stimulation, and by 58% after collagen stimulation in donor B (FIG. 14). Platelet aggregation induced by TRAP, ADP or AA was barely inhibited in donors A and B (FIG. 14).

In donor A, after 1 week Imbruvica (140 mg/d) platelet aggregation stimulated by two plaque homogenate pools was still inhibited by 94% and 91%, and after collagen stimulation by 91% (FIG. 15). In donor B, after intake of the very low dose of Imbruvica for 1 week (140 mg each other day), platelet aggregation stimulated by the two plaque homogenate pools was similarly inhibited by 93% and 91%, and after collagen stimulation by 82% (FIG. 15). Platelet aggregation induced by ADP or AA was barely inhibited in donors A and B (FIG. 15). Platelet aggregation stimulated by TRAP was reduced by 70% in donor A, and in donor B by 45%. Plaque-induced platelet aggregation was measured at several days during the weekly intake of Imbruvica (140 mg/d) by donor A. It was found to be inhibited >90% at each day tested (FIG. 16), independent, whether the blood for the measurements was taken 23 h or 3 h post dose.

Oral intake of Ibrutinib inhibited platelet thrombus formation under arterial flow conditions stimulated by plaque homogenate, but not by collagen (FIG. 17A,B). The loading dose of Imbruvica (3×140 mg) suppressed 3 h later plaque-induced thrombus formation equally well in both donors. After 1 week, both the low dose of Imbruvica 140 mg/d as well as the very low dose of Imbruvica 140 mg each other day suppressed plaque-induced thrombus formation, with slightly less inhibition observed after the very low dose of Imbruvica 140 mg (compare FIGS. 17A and B).

To test whether ibrutinib intake might increase bleeding time, the PFA-200 devices and the closure times were measured in both blood donors. Donor B and less donor A showed a prolonged closure time with the collagen/epinephrine test cartridge after 3 h after ibrutinib loading and 1 week after low dose ibrutinib intake (FIG. 18). It was noted that donor B had already closure time values above the normal range before ibrutinib intake. With the collagen/ADP Cartridge, closure time was in the normal range after ibrutinib intake both donors (FIG. 18).

Imbruvica intake (Imbruvica loading dose or weekly low dose intake) did not affect red cell, platelet and white blood cell (lymphocytes, neutrophils, monocytes) counts. B-lymphocytes (measured by FACS) were rather increased then decreased in both donors (Table 2). Liver enzymes were not altered by Imbruvica intake.

In conclusion, in two healthy volunteers an oral Imbruvica loading dose (3×140 mg) followed by a low maintenance dose (140 mg/d or 140 mg each other day) provided a rapid and continuous protection from plaque-induced platelet aggregation and platelet thrombus formation under arterial flow without adverse side effects.

TABLE 2

Effect of Imbruvica ® intake on blood counts of donor A and B

| | | Control | 3 h after Imbruvica loading dose | 1 week after low dose Imbruvica |
|---|---|---|---|---|
| Donor A | Red blood cells, ×10$^6$/µl | 4.2 | 4.07 | 4.22 |
| | Hb, g/dl | 12.8 | 12.4 | 13.0 |
| | HCT | 38.9 | 36.8 | 36.7 |
| | Platelets, ×10$^3$/µl | 233 | 247 | 217 |
| | Lymphocytes, % | 37.2 | 44 | 45.9 |
| | Monocytes, % | 6.9 | 5.8 | 8.1 |
| | Neutrophils, % | 55.9 | 50.2 | 46 |
| | Lymphocytes, ×10$^3$/µl | 1.8 | 2.6 | 2.9 |
| | Monocytes, ×10$^3$/µl | 0.3 | 0.3 | 0.5 |
| | Neutrophils, ×10$^3$/µl | 2.8 | 2.9 | 2.9 |
| | B-Lymphocytes, % | 12.5 | 14.0; 14.5 | 18.9; 18.5 |
| Donor B | Red blood cells, ×10$^6$/µl | 5.26 | 5.39 | 4.91 |
| | Hb, g/dl | 17.2 | 17.2 | 16.1 |
| | HCT | 46.4 | 47.8 | 44 |
| | Platelets, ×10$^3$/µl | 179 | 188 | 160 |
| | Lymphocytes, % | 31.2 | 27.0 | 29.5 |
| | Monocytes, % | 9.4 | 10.7 | 12.5 |
| | Neutrophils, % | 59.4 | 62.3 | 58 |
| | Lymphocytes, ×10$^3$/µl | 1.7 | 1.7 | 2.0 |
| | Monocytes, ×10$^3$/µl | 0.5 | 0.7 | 0.9 |
| | Neutrophils, ×10$^3$/µl | 3.3 | 4.0 | 3.9 |
| | B-Lymphocytes, % | 6.2; 6.0 | 7.0; 7.3 | 8.6; 8.5 |

The invention claimed is:

1. A method of treating and/or preventing atherothrombosis in a subject in need thereof, comprising administering a pharmaceutically effective amount of an inhibitor of Bruton's tyrosine kinase (Btk) to the subject, wherein the inhibitor of Btk is a small molecule inhibitor that comprises an azole motif and/or an azine motif, and the pharmaceutically effective amount of the inhibitor of Btk suppresses atherosclerotic plaque-induced platelet aggregate formation and does not have a significant effect on collagen-induced platelet aggregate formation under arterial flow conditions in the subject.

2. The method of claim 1, wherein the inhibitor irreversibly binds to Btk.

3. The method of claim 1, wherein the inhibitor is ibrutinib, acalabrutinib (ACP-196), ONO/GS-4059, or BGB-3111.

4. The method of claim 1, wherein the inhibitor is comprised in a pharmaceutical composition, optionally further comprising a pharmaceutically acceptable carrier, excipient and/or diluent.

5. The method of claim 1, wherein the inhibitor is administered at a loading dose of 280 to 560 mg, and a maintenance dosage of 10 to 140 mg per day or 40 to 280 mg each other day.

* * * * *